United States Patent
Steffens

(10) Patent No.: US 12,306,149 B2
(45) Date of Patent: May 20, 2025

(54) METHOD FOR THE DETECTION AND QUANTIFICATION OF ADENO-ASSOCIATED VIRUSES (AAVs) USING AN AFFINITY MATRIX

(71) Applicant: Sartorius Xell GMBH, Schloß Holte-Stukenbrock (DE)

(72) Inventor: Tim Steffens, Bielefeld (DE)

(73) Assignee: Sartorius Xell GMBH, Schloß Holte-Stukenbrock (DE)

( * ) Notice: Subject to any disclaimer, the term of this patent is extended or adjusted under 35 U.S.C. 154(b) by 0 days.

(21) Appl. No.: 18/443,262

(22) Filed: Feb. 15, 2024

(65) Prior Publication Data
US 2024/0255475 A1    Aug. 1, 2024

Related U.S. Application Data

(63) Continuation of application No. PCT/EP2023/051396, filed on Jan. 20, 2023.

(30) Foreign Application Priority Data

Jan. 20, 2022 (EP) ..................................... 22152560
Jun. 24, 2022 (EP) ..................................... 22181004

(51) Int. Cl.
*G01N 30/74* (2006.01)
*G01N 30/02* (2006.01)
*G01N 33/68* (2006.01)

(52) U.S. Cl.
CPC ......... *G01N 30/74* (2013.01); *G01N 33/6827* (2013.01); *G01N 2030/027* (2013.01); *G01N 2333/015* (2013.01)

(58) Field of Classification Search
None
See application file for complete search history.

(56) References Cited

U.S. PATENT DOCUMENTS

2021/0009964 A1* 1/2021 Khatwani ............ B01D 15/166
2021/0187049 A1   6/2021 Curtis et al.

FOREIGN PATENT DOCUMENTS

| WO | WO 2017/100704 | * | 6/2017 |
| WO | WO-2019/212922 A1 | | 11/2019 |
| WO | WO-2020061581 A1 | | 3/2020 |
| WO | WO 2021/062164 | * | 4/2021 |
| WO | WO 2021/231296 | * | 11/2021 |
| WO | WO-2021/231296 A1 | | 11/2021 |

OTHER PUBLICATIONS

Thermoscientific™ Publication No. 100038399, POROS™ CaptureSelect™ AAV Resins: AAV8, AAV9, AAVX, available online Apr. 26, 2016.*
Tustain et al. (Biotechnology and Bioengineering. Nov. 2021; 118(11):4186-203).*
Kessenbrock and Groth "Circular dichroism and fluorescence spectroscopy to study protein structure and protein-protein interactions in ethylene signaling". Ethylene Signaling: Methods and Protocols. 2017:141-59.*
Xie et al. (Analytical Biochemistry. Sep. 2023; 680: 115311).*
Pete Gagnon, et al., "Multiple-Monitor HPLC Assays for Rapid Process Development, In-Process Monitoring, and . . . ", Pharmaceutics, 2021, p. 113, vol. 13, No. 1.
Benjamin Adams, et al., "Moving from the Bench Towards a Large Scale, Industrial platform . . . ", Biotechnology and Bioengineering, 2020, pp. 3199-3211, vol. 117, No. 10.
Aravind Asokan, et al., "The AAV Vector Tool: Poised at the Clinical Crossroads", Molecular Therapy, 2012, pp. 699-708, vol. 20, No. 4.
Lutz Fischer and Timo Stressler, "Chapter 2: Protein Determination", In: Bioanalytics, 2018, pp. 23-33, F. Lottspeich & J. Engles, eds., Wiley-VCH, Weinheim, Germany.
Andreas L. Gimpel, et al., "Analytical Methods for Process and Product Characterization . . . ", Molecular Therapy: Methods & Clinical Development, 2021, pp. 740-754, vol. 20.
Anita F. Meier, et al., "The Interplay Between Adeno-Associated Virus and its Helper Viruses", Viruses, 2020, p. 662, vol. 12, No. 6.
"POROS CaptureSelect AAV9 Resins: AAV8, AAV9, AAVX", ThermoFisher Scientific, 2017, pp. 1-8, Publication No. 100038399, Rev. E.
Thomas Quast, et al., "Chapter 8: Light Microscopy Techniques—Imaging", In: Bioanalytics, 2018, pp. 181-206, F. Lottspeich & J. Engles, eds., Wiley-VCH, Weinheim, Germany.
Dan Wang, et al., "Adeno-Associated Virus Vector as a Platform for Gene Therapy Delivery", Nature Reviews: Drug Discovery, 2019, pp. 358-378, vol. 18, No. 5.

* cited by examiner

*Primary Examiner* — Shanon A. Foley
(74) *Attorney, Agent, or Firm* — Grimes & Yvon LLP

(57) ABSTRACT

The present invention relates to a method for the detection of the capsid titer of an adeno-associated virus (AAV) and to a method for the determination of the ratio of full and empty capsids of an AAV by the use of an affinity matrix.

22 Claims, 15 Drawing Sheets

Figure 3

Figure 1:
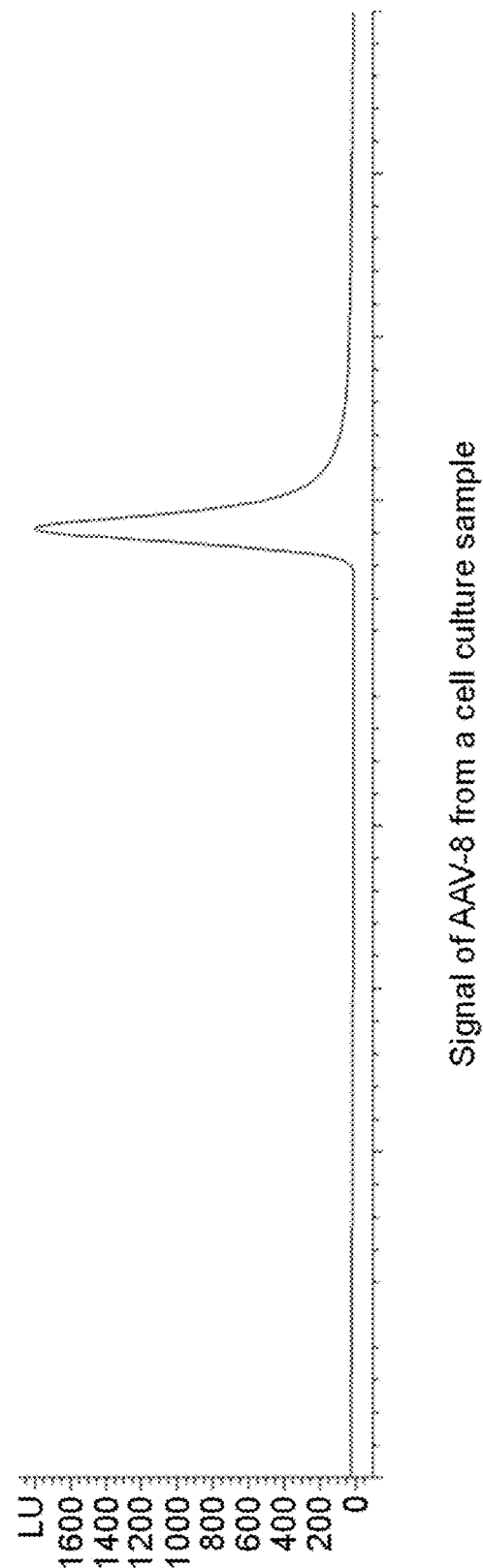

| AAV-8 containing culture sample | Capsid titer per mL (Affinity chromatography) | Deviation of affinity chromatography to reference ELISA [%] | CV | CV total |
|---|---|---|---|---|
| Aliquot A, day 1 | 4.33E+12 | 7.2 | 2.4 | 2.2 |
| Aliquot B, day 1 | 4.53E+12 | 3.0 | | |
| Aliquot C, day 1 | 4.58E+12 | 1.9 | | |
| Aliquot D, day 2 | 4.34E+12 | 7.0 | 0.9 | |
| Aliquot E, day 2 | 4.42E+12 | 5.4 | | |

Figure 4

|  | total Capsids | Volume |
|---|---|---|
| Sum fraction collected from 3 mL Culture | 1.20E+13 | 1.5 mL |
| Sum Culture (3 mL) | 1.40E+13 | 3 mL |
| Recovery | 86% | |

Figure 6

| AAV-5 containing culture sample, quantified with AAV-8 reference samples | Capsid titer per mL (Affinity chromatography) | Deviation of affinity chromatography to reference ELISA [%] | CV |
|---|---|---|---|
| Aliquot A, day 1 | 7.02E+11 | 3.9 | 1.6 |
| Aliquot B, day 2 | 6.80E+11 | 0.6 | |

Figure 8

|  | Capsid (FLD) | VG (UV260) | Empty/Full (%) |
|---|---|---|---|
| AAV8 | 1.51E+12 | 5.88E+10 | 4 |

Figure 9

|  | Capsids/mL ||
| --- | --- | --- |
|  | Affinity LC | ELISA |
| AAV8 Ultrafiltration | 1.27E+12 | 1.34E+12 |
| AAV8 Culture Supernatant | 1.342E+12 | 1.46E+12 |
| AAV5 Culture Supernatant | 6.80E+12 | 6.76E+12 |

Figure 11

A

| Crude extract | Total capsids | | | Full capsids / VG | | | | Empty/Full Ratio | | |
|---|---|---|---|---|---|---|---|---|---|---|
| Sample | SEC-MALS* | Affinity (in-house) | ELISA | SEC-MALS* | Affinity (in-house) | ddPCR | SEC-MALS* | Affinity (in-house) | ddPCR/ELISA |
| AAV8 protocol 1 | 4.00E+12 | 5.66E+12 | 4.06E+12 | 1.92E+11 | 2.04E+11 | 2.76E+11 | 4.8% | 3.6% | 6.1% |
| AAV8 protocol 2 | 3.89E+12 | 4.99E+12 | 5.12E+12 | 2.05E+11 | 2.00E+11 | 2.66E+11 | 5.3% | 4.0% | 5.2% |
| AAV2 protocol 1 | N/A | 2.89E+12 | 3.47E+12 | N/A | 6.08E+10 | 1.51E+10 | N/A | 2.1% | 0.6% |
| AAV2 protocol 2 | N/A | 2.46E+12 | 4.68E+12 | N/A | 5.67E+10 | 1.27E+10 | N/A | 2.3% | 2.8% |
| AAV5 protocol 1 | N/A | 2.55E+12 | 5.78E+12 | N/A | 1.37E+11 | 2.36E+11 | N/A | 5.2% | 3.9% |
| AAV5 protocol 2 | N/A | 2.34E+12 | 5.98E+12 | N/A | 1.10E+11 | 2.36E+11 | N/A | 4.7% | 4.2% |

*SEC-MALS is better used for purified samples and was therefore only applied to AAV8 as proof of concept.

B

| Purified Extract | Total capsids | | Full capsids / VG | | Empty/Full Ratio | |
|---|---|---|---|---|---|---|
| Sample | SEC-MALS | Affinity (in-house) | SEC-MALS | Affinity (in-house) | SEC-MALS | Affinity (in-house) |
| AAV5 protocol 1 | 1.80E+12 | 1.10E+12 | 6.98E+10 | 4.47E+10 | 3.9% | 4.0% |
| AAV5 protocol 2 | 1.90E+12 | 1.15E+12 | 6.12E+10 | 4.81E+10 | 3.2% | 4.2% |

METHOD FOR THE DETECTION AND QUANTIFICATION OF ADENO-ASSOCIATED VIRUSES (AAVs) USING AN AFFINITY MATRIX

CROSS-REFERENCE TO RELATED APPLICATIONS

This application is a continuation of International Application No. PCT/EP2023/051396, filed on Jan. 20, 2023, which claims the benefit and priority of European Patent Application No. 22152560.3, filed on Jan. 20, 2022, and of European Patent Application No. 22181004.7, filed on Jun. 24, 2022, the contents of each of which are herein incorporated by reference in their entirety.

FIELD OF INVENTION

The present invention relates to a method for the detection of the capsid titer of an adeno-associated virus (AAV) and to a method for the determination of the ratio of full and empty capsids of an AAV by the use of an affinity matrix.

BACKGROUND OF THE INVENTION

Adeno-associated viruses (AAVs) are linear, single-stranded DNA viruses that belong to the Parvovirus family. The AAVs are infectious to cells of a wide range of species including human and also infect non-dividing cells in which differentiation is terminated such as blood cells, muscle cells, or neural cells. Wild-type AAVs are not pathogenic to human. Also, the AAVs are very stable physicochemically. From these features, AAVs are widely used vectors for in vivo gene therapy. Their therapeutic applicability is primarily because of their non-pathogenicity to humans, low immunogenicity and long-term gene expression (Gimpel et al., Molecular Therapy: Methods & Clinical Development (2021), Vol. 20, pp. 740-754). Moreover, AAVs are particularly safe because AAVs cannot replicate on their own, and the vector is maintained as an episome instead of directly integrating into a host genome. Furthermore, AAVs can target different tissue or cell types depending on the composition of its capsid proteins, making it an attractive candidate for delivery of gene therapies in vivo (Wang et al., Nat Rev Drug Discov. (2021), Vol. 18 (5), pp. 358-378).

The development of AAVs requires identification of critical quality attributes (CQAs) of the product and characterization of the functional relationship between CQAs and process parameters. The CQAs indicate the product's identity, potency, purity, and safety (Gimpel et al., Molecular Therapy: Methods & Clinical Development (2021), Vol. 20, pp. 740-754). One important CQA of AAVs is the AAV capsid titer. The AAV capsid titer is crucial for the operation and optimization of downstream recovery or purification processes that depend on the load of product rather than its potency, e.g., loading of preparative columns, or pooling of column fractions. For the detection and quantification of the AAV capsid titer, available methods can be broadly categorized as antibody-based or optical methods. Whereas both groups achieve similar levels of repeatability, antibody-based methods trade a longer turnaround for high specificity and vice versa. Especially, conventional enzyme-linked immunosorbent assay (ELISA), the most established method for capsid quantification, is laborious, requires 3 to 4 hours to complete, but reliably quantifies non-purified in-process samples, albeit the method suffers from a poor accuracy and precision. Gimpel et al. reports that the quantification limit in ELISA methods is around 10E+8 capsid particles (cps) per milliliter (Gimpel et al., Molecular Therapy: Methods & Clinical Development (2021), Vol. 20, pp. 740-754). Moreover, WO 2019/212922 A1 discloses methods for the determination of genome content, capsid content and full/empty ratios of AAV particles by UV absorbance.

Another commonly used method for the quantification of the AAVs is the size-exclusion chromatography (SEC) combined with a multi-angle light scattering (MALS) (hereinafter referred to as SEC-MALS). With SEC-MALS, detection of capsid titer and the content ratio is possible for purified samples only (Gimpel et al., Molecular Therapy: Methods & Clinical Development (2021), Vol. 20, pp. 740-754). The content ratio, as the second potential CQA, refers to the ratio of AAV capsids either missing or having a partial genome, termed empty or partially-filled capsids, respectively, and represents the most common product-related impurity in AAV production methods (Gimpel et al., Molecular Therapy: Methods & Clinical Development (2021), Vol. 20, pp. 740-754). The currently most widely used methods for the determination and quantification of the genome titer are quantitative polymerase chain reaction (qPCR) and digital droplet PCR (ddPCR): both methods quantify the DNA content via fluorescence during or after amplification in a thermocycler. Fluorescent reporters used in qPCR and ddPCR include double-stranded DNA (dsDNA)-binding dyes, or dye molecules attached to PCR primers or probes that hybridize with the PCR product during amplification. For accuracy, these methods require chemical or enzymatic treatment of the sample to digest non-encapsidated DNA and denature capsid proteins to expose the encapsidated DNA (Gimpel et al., Molecular Therapy: Methods & Clinical Development (2021), Vol. 20, pp. 740-754). A key challenge for antibody-based methods such as the ELISA remains the need for serotype-specific antibodies, which are presently only available for the most common serotypes. Further, SEC-MALS requires a stringent purification protocol in order to render the AAV samples accessible for the analysis. Thus, SEC-MALS methods are unable to characterize non-purified samples, i.e. requiring prior purification. Moreover, the PCR-based methods have important limitations as the PCR-based methods are indifferent toward the integrity of the vector genome, as both complete and truncated genomes with intact amplicon contribute to the genome titer. Needless to say that with PCR methods it is not possible to determine the capsid protein titer because these methods require chemical or enzymatic treatment of the sample to digest non-encapsidated DNA and denature capsid protein to expose the encapsidated DNA.

Therefore, methods are required for the detection of the capsid titer and content ratio of AAVs, which overcome the drawbacks of the prior art methods. In particular, methods are required which allow the detection of the total capsid content and/or the quantification of the content ratio of AAVs of samples in an efficient and reliable manner.

SUMMARY OF INVENTION

This need is addressed by the present invention by providing the embodiments as defined in the claims.

The present invention relates to methods for the detection of the AAV capsid titer. The AAVs comprise protein capsid having three capsid proteins (VP1, VP2, and VP3) and a single-stranded DNA genome surrounded therewith. The genome of the wild-type AAVs has a nucleotide sequence forming a T-shaped hairpin structure called ITR (Inverted Terminal Repeat) at both terminals, and a half of the linear single-stranded genome between the terminals encodes Rep protein (rep gene), and the remainder half encodes a capsid protein (cap gene). At least thirteen serotypes (AAV 1-13) have been known to date as wild-type AAVs which are infectious to human.

Typical recombinant adeno-associated viral vectors (rAAV vectors) have a genome structure in which rep gene and cap gene of the AAV genome are replaced by desired genes and the like. One example of the method for preparing an rAAV vector includes a method comprising introducing into host cells such as HEK293 cells collectively a vector plasmid in which an intended gene is inserted between ITRs of the AAV, a helper plasmid for supplying the viral proteins in need for replication of the AAV or formation of viral particles, and an adenovirus helper plasmid, to produce rAAV vectors in the nucleus of the host cells. Methods for producing rAAV vectors are well known in the art (see e.g. Meier et al., Viruses (2020), Vol. 12 (6), 662). Other examples of host cells, such as Sf9 insect cells, Hela cells or baby hamster kidney (BHK) cells for preparing rAAV vectors are known in the art. When the rAAV vector(s) is (are) used for gene transduction of the cells, it is necessary to prepare (an) rAAV vector(s) having a sufficiently high titer. Therefore, the determination of the titer is essential in the preparation of the rAAV vector(s).

Although large-scale AAV affinity columns are on the market for the purification of AAV capsids, these columns are not suitable for the detection of the capsid titer of AAV. These columns are used to gain the highest possible yield, therefore they possess the feature to bind a vast amount of AAV particles. These originate most likely from bigger amounts of a cell culture process or even the whole culture batch. This purification application is contrary to an analytical application, because an analytical application uses only small amounts of sample in order to gain knowledge on a certain stage during a cultivation. In summary, an analytical method accompanies a process to gain information, while a preparative process is intended to gain a product. Furthermore, it is not possible to simply use a preparative column for an analytical task. Further, large-scale AAV affinity columns may suffer of so-called rebinding effects. Rebinding effects occur when the matrix is strongly undersaturated with the AAV so that the dissociated AAV may bind several times onto the matrix. Accordingly, the present invention is based on the development of a method for the detection and quantification of AAVs using an affinity matrix. In contrast to preparative methods that are solely used for down-stream processing, analytical methods are used to gain information about a given sample (here an AAV sample). When that sample contains AAV, the titer of the capsid proteins as well as genomes are of interest. While there are preparative affinity columns available for AAV samples, no analytical scale column could be found. Therefore, to determine the AAV titer, different methods and sometimes clean-up procedures have to be performed: ELISA and PCR methods, such as digital droplet polymerase chain reaction (ddPCR) or quantitative polymerase chain reaction (qPCR), or the like has been utilized (see (Gimpel et al., Molecular Therapy: Methods & Clinical Development (2021), Vol. 20, pp. 740-754). These state-of-the art technologies such as ELISA, analytical ultracentrifugation (AUC) and static light scattering/dynamic light scattering (SLS/DLS) suffer from several drawbacks including long turnaround and throughput, large and pure sample quantities, labor intensity, poor reproducibility, sample destruction, serotype specificity. These drawbacks have been solved by the present invention, particularly by the use of an affinity matrix, preferably in an HPLC process, as a tool for the detection of the AAV capsid titer and the determination of the content ratio of the AAV capsids (i.e. to determine whether the AAV capsids are full capsids, partially-filled or empty capsids).

Accordingly, the present invention relates to a method for the detection of the capsid titer of an adeno-associated virus (AAV), wherein the method comprises the following steps:
(a) loading an AAV sample onto an affinity matrix;
(b) eluting the AAV from the affinity matrix; and
(c) detecting the AAV capsid titer in the eluate with a fluorescence detection system.

In the context of the present invention, the intrinsic fluorescence of the aromatic amino acids in the AAV capsids proteins is measured. Excitation of the fluorescent groups in the proteins generally takes place at an excitation wavelength of between 200 nm and 290 nm, preferably 280 nm, and the determination of the emission values is in the range of 320 to 350 nm, preferably between 340 nm and 350 nm, most preferably at 350 nm. Furthermore, the present invention relates to a method for the detection of the content ratio, referring to the ratio of AAV capsids missing, having a partial genome, or a full genome (termed empty, partially-filled or full capsids) of (an) AAVs. Accordingly, the present invention also relates to a method for the determination of the content ratio of the AAV capsids, wherein the method comprises the following steps:
(a) loading an AAV sample onto an affinity matrix;
(b) eluting the AAV from the affinity matrix; and
(c) detecting the AAV in the eluate with a fluorescence detection system and with an UV spectrophotometry method thereby determining the ratio of full and empty capsids of the AAV.

As shown in the appended Examples, the methods as defined in the claims ensure to gain information about a sample that contains AAV (AAV sample), whereby the capsid titer as well as the content ratio is of particular interest. In contrast to commonly used methods such as SEC-MALS for the detection of the capsid titer and the content ratio, the methods of the present invention allows the direct usability of the samples, i.e. non-purified samples can be directly loaded onto the affinity matrix so that no clean-up procedures have to be performed. Thus, the methods of the present invention do not necessarily comprise the step of purifying and/or centrifuging the sample before loading onto the affinity matrix. In other words, the methods of the present invention are particularly useful for non-purified samples because the usability of an affinity matrix allows the simultaneous detection of the capsid titer and purification of the non-purified samples. As shown in Example 5, the methods of the present invention separate the desired AAV particles from the original cell culture sample (AAV sample) thereby separating impurities such as host cell proteins (HCPs) from the AAV sample. Thus, the claimed method is superior compared to the commonly used methods such as SEC-MALS because the methods of the present invention save time and resources.

Another advantage over commonly used methods is that the presented methods are non-destructive, i.e. the detected native AAV particles might be collected after detection and then used for further applications. In the methods of the present invention, the intrinsic fluorescence of the aromatic amino acids in the AAV capsids proteins is measured. Intrinsic protein fluorescence derives mostly from tryptophan residues, with a much lesser contribution by tyrosine and still less by phenylalanine; see, e.g., Chapter 2.2.2, Table 2.6 in the textbook "Bioanalytics", Eds. F. Lottspeich, J. W.

Engels, (2018), ISBN 9783527339198. Tryptophan is remarkably abundant in AAV capsids proteins, constituting 2.2% of complete capsids; see UniProtKB-P03135 (CAPSD_AAV2S). See also Gagnon et al., Pharmaceutics 13, 113, pp. 2 to 14 (2021). This enables that the AAV capsids proteins can be detected by the measurement of the intrinsic fluorescence. This is in sharp contrast to the method disclosed in WO 2021/231296 A1 where the fluorescence detection is derived from labelled AAV capsids proteins. The claimed methods fundamentally differ from the method of WO 2021/231296 A1 where a preparation step is necessary to label the AAV capsids proteins before they can be determined with a fluorescence detection system. Thus, WO 2021/231296 A1 discloses methods where labelled AAV capsids proteins were measured, whereas the claimed methods allow the detection and determination of unmodified, naturally present AAV capsids proteins in an AAV sample. Additionally, WO 2021/231296 A1 does not disclose methods that determine the intrinsic fluorescence of the AAVs. To the contrary, the fluorescent moieties (eGFP) used in the Examples of WO 2021/231296 A1 have an absorption maximum of about 395 nm and an emission maximum of about 475 nm; see, e.g., Chapter 8.4, Table 8.2 in the textbook "Bioanalytics", Eds. F. Lottspeich, J. W. Engels, (2018), ISBN 9783527339198.

Figure 10:
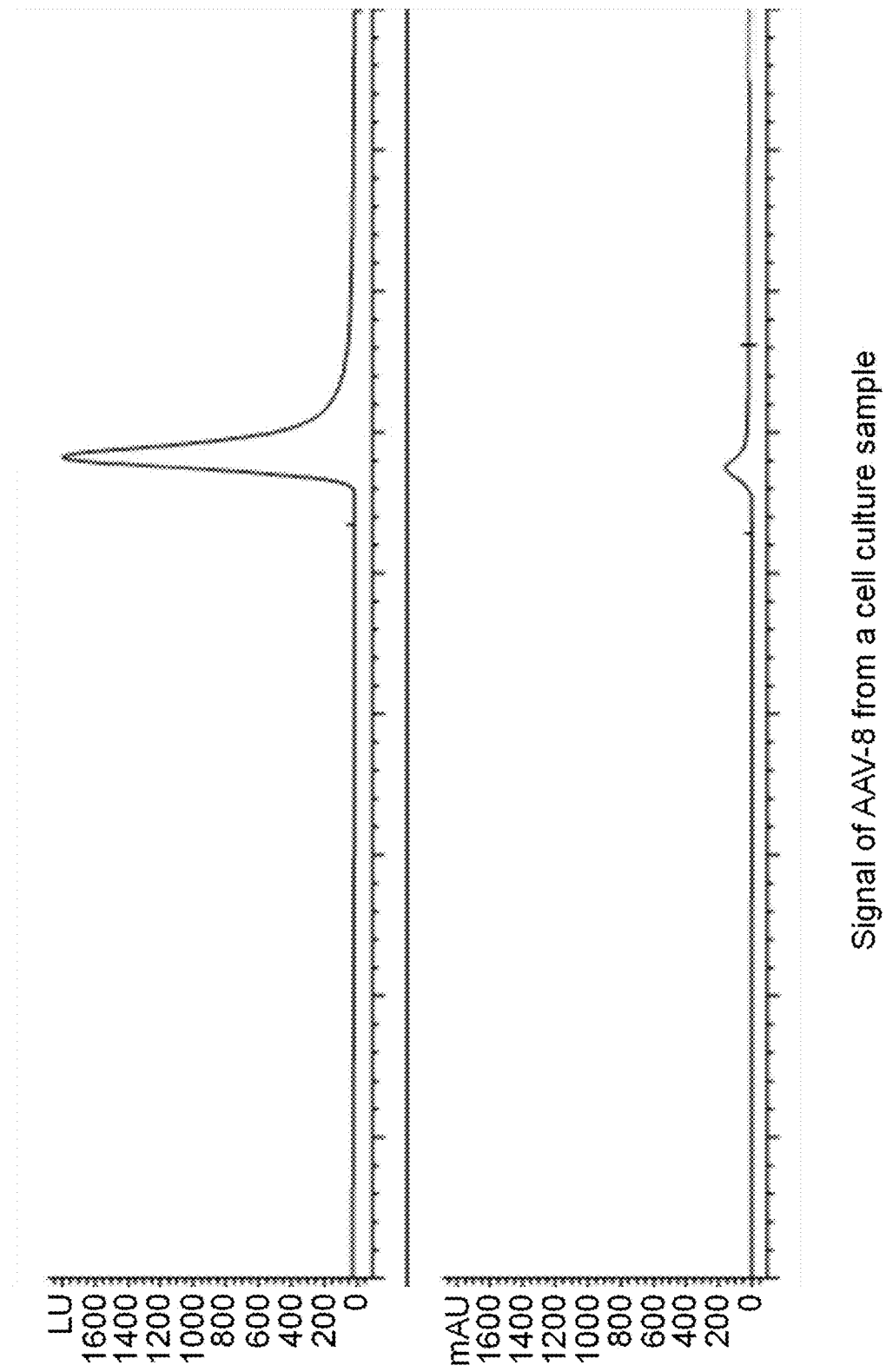

Furthermore, the determination of the intrinsic fluorescence of the AAV proteins capsids has a higher sensitivity as compared to the UV detection. Example 9 of the appended Examples directly compares the capsid detection via fluorescence detection (FLD) and UV detection (UV). In this Example 2E+12 capsids were applied to the method and detected either via FLD (280 nm→350 nm) or UV (280 nm). As evident from FIG. 10, the same sample resulted in two different signals with the fluorescence signal being stronger. Thus, as shown in FIG. 10, the detection via fluorescence is superior compared to the UV absorption at 280 nm.

Figure 12:
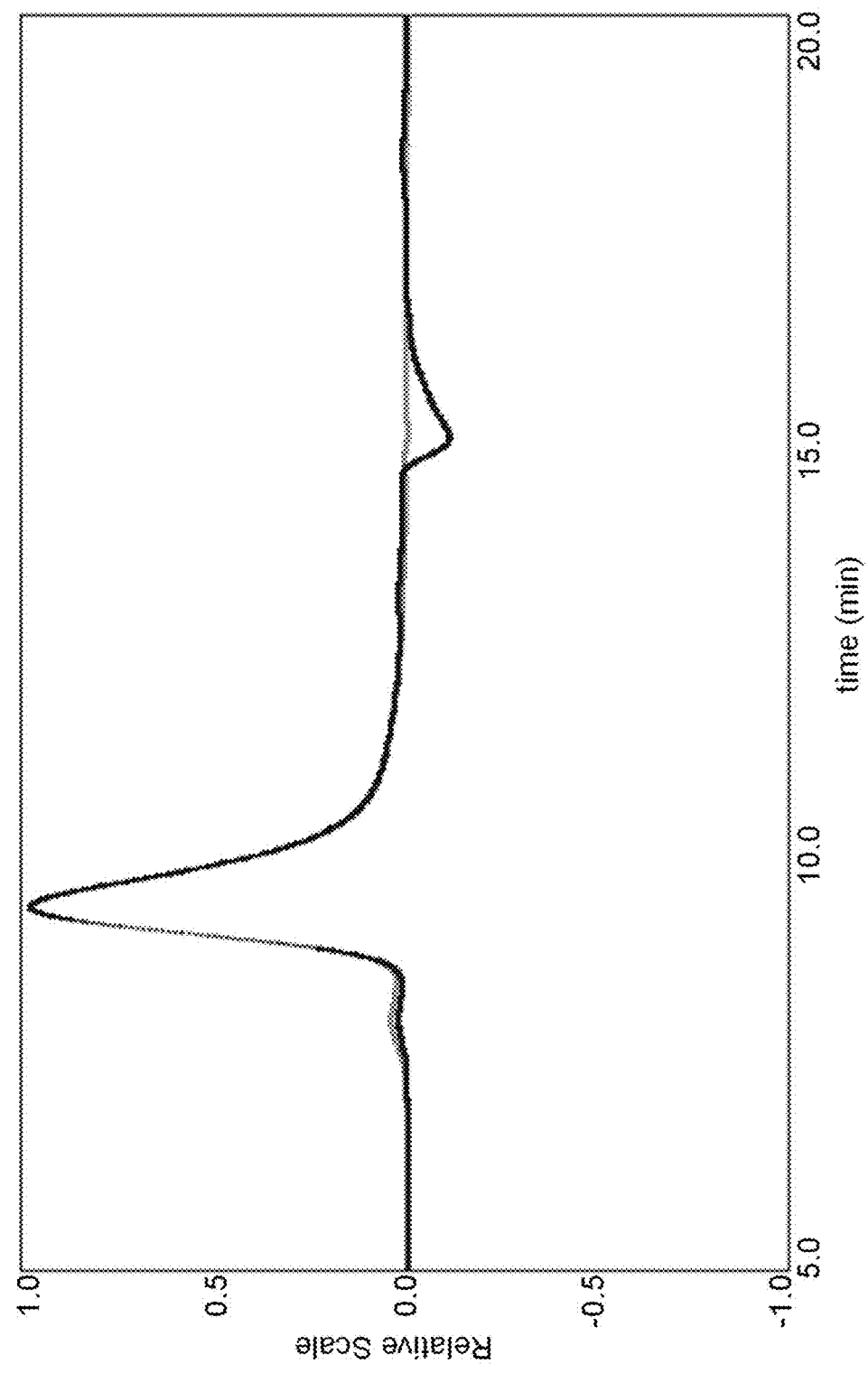
Figure 12:
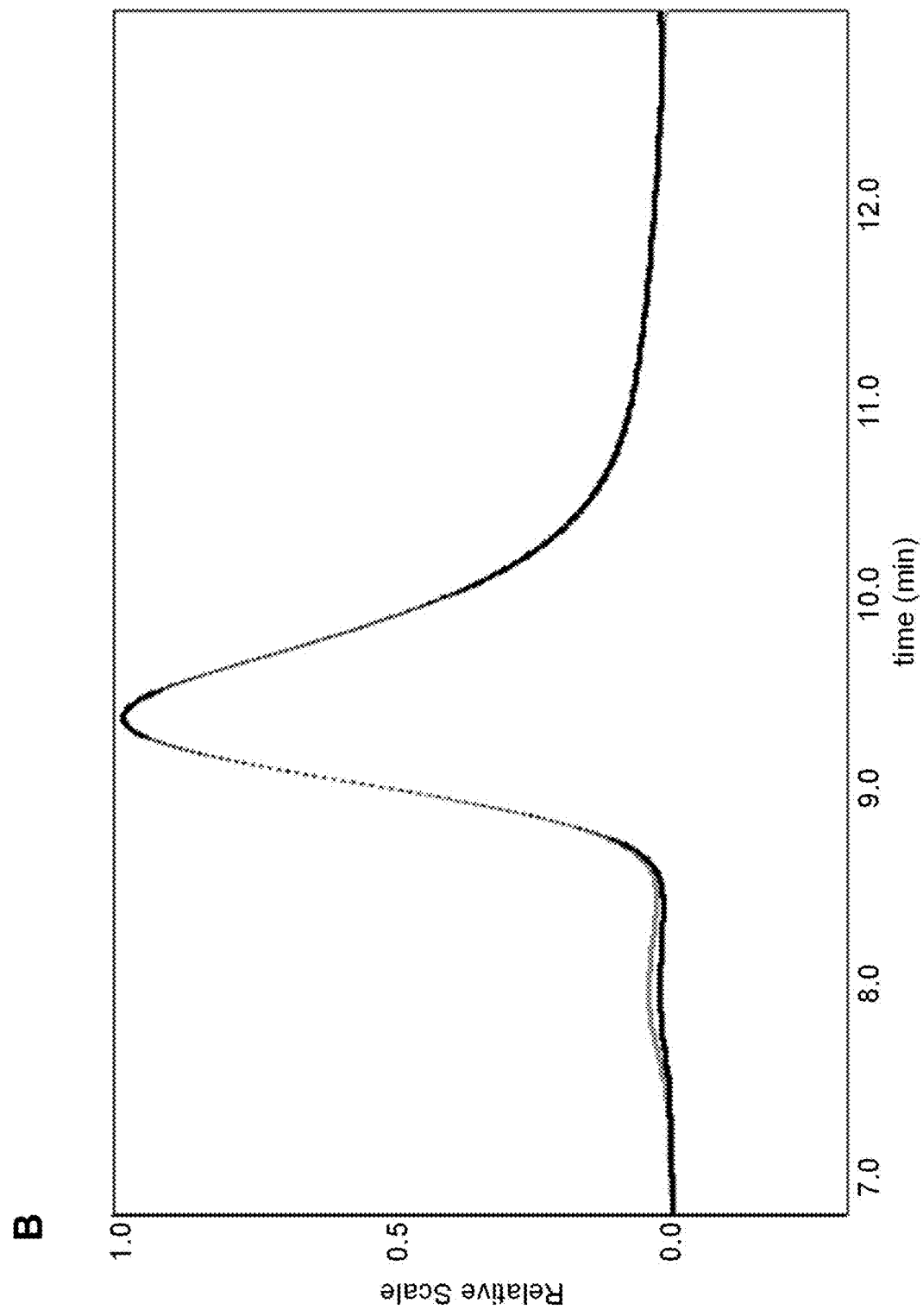
Figure 13:
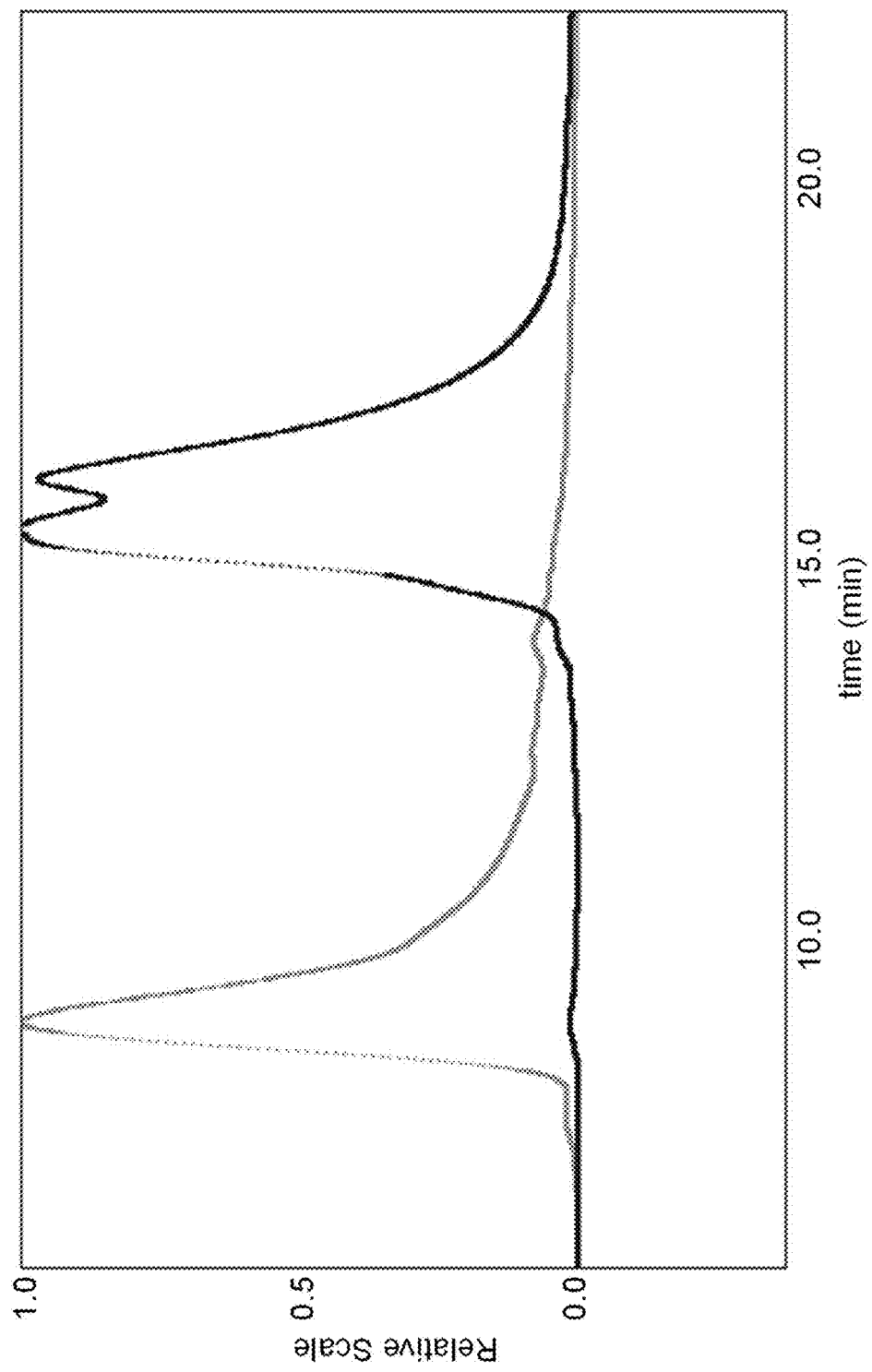
Figure 13:
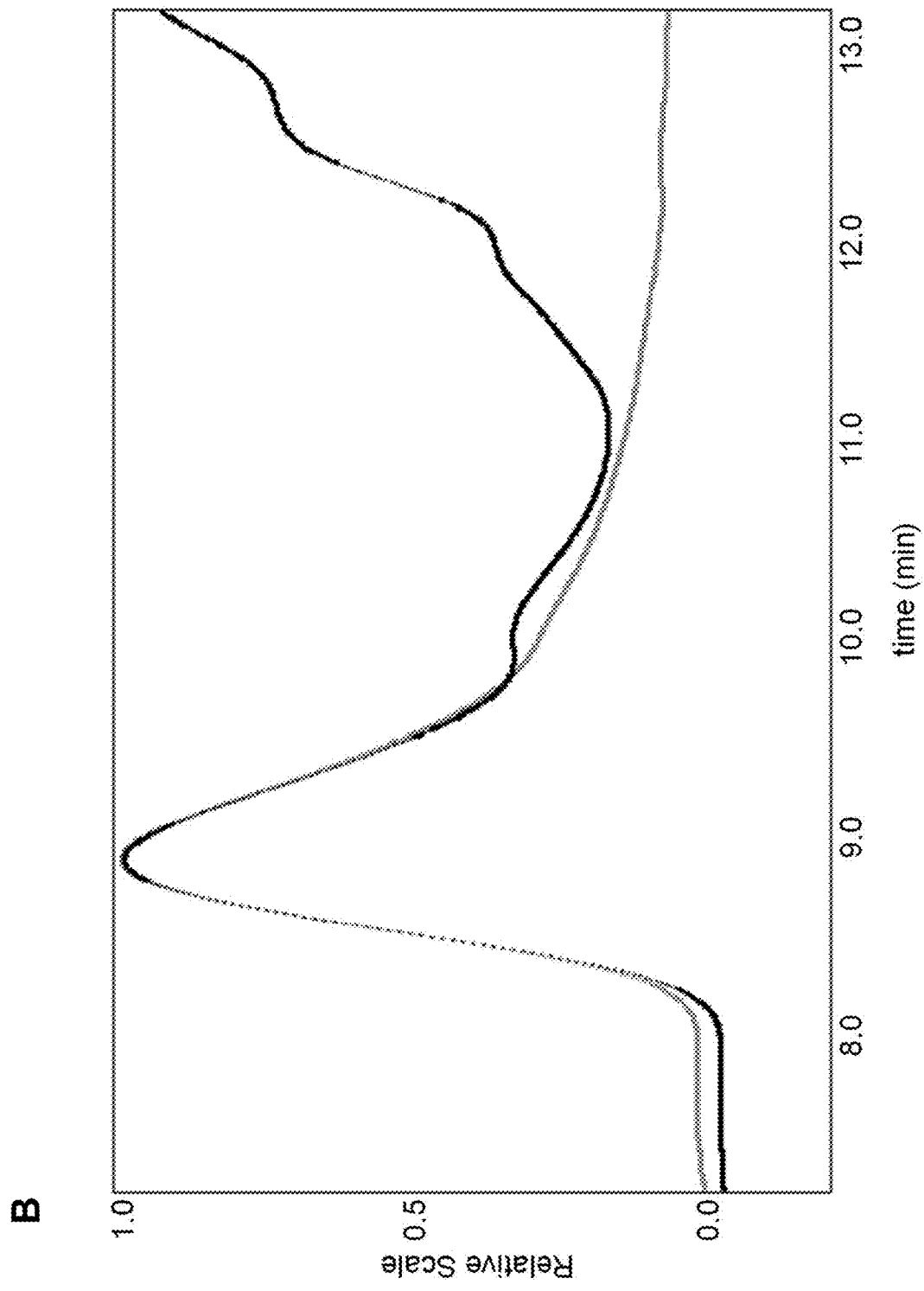

Thus, the data of the original application demonstrate that the claimed methods are superior and fundamentally different to methods for the detection of AAV capsids that use chromatographic separation methods such as cation exchange chromatography (CEA), anion exchange chromatography (AEC), or size exclusion chromatography (SEC). As will be explained in more detail below and as exemplified in the appended Examples, the claimed methods use affinity chromatography for the purification and detection of the AAV capsids. This is fundamentally different to the methods that use CEA, AEC or SEC and is advantageous compared to these chromatography methods because it allows the detection of AAV capsids in an AAV sample in a small-scale process and a non-destructive manner; see also Example 10. FIGS. 12 and 13 of Example 10 also show that the invented method can not only be used for direct analysis of the native AAV capsids, but also subsequent methods like SEC-MALS can be applied.

ELISA is the most established method for the detection of capsid titers. However, it possesses several drawbacks. As evident from Example 3, the methods of the present invention allow the quantification of samples with a titer above 4E+12 capsids per ml without diluting the sample. In contrast, the quantification limit in ELISA methods is around 10E+8 (see Gimpel et al., Molecular Therapy: Methods & Clinical Development (2021), Vol. 20, pp. 740-754), thus indicating that the sample needs to be diluted to the range suitable for ELISA, since AAV processes are expected to result in titers above 10E+8 capsids per ml. Furthermore, the ELISA works through an indirect detection of the AAV that is carried out by a colorimetric reaction for which several binding steps are essential. Therefore, the ELISA needs to be performed with fixed volumes and strictly according to protocol, including several wash steps and binding reactions, in order to work, making it error prone. In contrast, the here presented methods allow the use of various amounts of sample, since the used volume can be taken into account during quantification. Likewise, the coefficient of variation (CV) is better than the one of ELISAs: Example 3 reports that the claimed methods are characterized by a repeatability of 2.2 (less than 10%), whereas the ELISA methods have a repeatability of 10 to 20% CV; see Gimpel et al., Molecular Therapy: Methods & Clinical Development (2021), Vol. 20, pp. 740-754). In consequence, the claimed methods are advantageous compared to ELISA (i.e. the state-of-the art technology for the determination of the capsid titer). Moreover, as shown in the Examples, the claimed methods provide a good and reliable outcome with a sample volume of 0.5 ml (non-purified) in 30 minutes. As mentioned above, conventional ELISA requires 3 to 4 hours to complete.

Likewise, the claimed methods are also superior compared to chromatography systems such as ÄKTA™ commonly used for preparative purification. In preparative purification processes sample volumes of at least 15 ml are commonly used with the aim to obtain a purified sample. Typically, sample volumes of preparative purification processes range from hundreds of ml to multiple or hundreds of liters. Thus, preparative purification methods have only the intention to purify the protein of interest from impurities. Furthermore, Example 9 of the appended Examples directly compares the capsid detection via fluorescence detection (FLD) and UV detection (UV). In this Example 2E+12 capsids were applied to the method and detected either via FLD (280 nm→350 nm) or UV (280 nm). As evident from FIG. 10, the same sample resulted in two different signals with the fluorescence signal being stronger. Thus, as shown in FIG. 10, the detection via fluorescence is superior compared to the UV absorption at 280 nm. In contrast, large-scale preparative chromatography systems such as ÄKTA™ may use UV absorption for monitoring the preparative affinity clean-ups, specifically to determine the product and waste fractions, but not for the detection or quantification.

Needless to say that the use of small sample volumes as used in the methods of the present invention as compared to preparative purification methods is particularly advantageous for the industry. The use of small sample volumes is particularly useful in the development of small-scale processes. For example the claimed methods could be used during a virus production process where small AAV samples are taken on a regular basis during a virus production process, e.g., when infecting the cells, day 1 after the infection, day 2 after the infection etc. Likewise, a further useful application of the methods of the present invention may lay in the field of the quality control. For instance, the methods of the present invention may be used in formulated rAAVs just prior to application in order to assure that the virus titer is correct. Thus, the claimed methods are superior compared to the state-of-the art methods (such as ELISA, SEC-MALS and preparative purification methods) and are of industrial relevance.

The methods of the present invention use affinity chromatography for the detection and separation of the AAV capsid titer of an AAV sample. Affinity chromatography is performed on stationary phases containing immobilized biomimetic or biospecific ligands and separates proteins according to principles of molecular recognition. Affinity chromatography is highly selective and has a higher binding capacity for the protein of interest (here: AAV capsid protein) than anion exchange chromatography (AEC), cation exchange chromatography (CEA), or size exclusion chromatography (SEC). In AEC, proteins are separated according to their net negative charge, whereby the retaining mobile phase is aqueous, of high pH, and low salt concentration and the eluting mobile phase is either aqueous, of high pH and high salt concentration, or aqueous and of low pH. CEA separates analytes according to their net positive charge, whereby the retaining mobile phase is aqueous, of low pH, and low salt concentration and the eluting mobile phase is either aqueous, of low pH and high salt concentration, or aqueous and of high pH. In SEC, proteins are separated according to their molecular mass. Again, for the sake of repetition, affinity chromatography is used in the methods of the present invention. Accordingly, the detection and determination of the capsid titer is done in the methods of the present invention by an affinity matrix. In the context of the present invention, the term "affinity matrix" refers to a resin that can undergo a ligand-biomacromolecule interaction with the AAV during the process. In the context of the present invention, the affinity matrix preferably comprises a solid support and an immobilized ligand bound to the solid support. In the context of the present invention, the immobilized ligand binds to a specific AAV serotype, any mixture of AAV serotypes, or a AAV serotype derivate from (any) AAV serotype(s). Moreover, in the context of the present invention, the ligands may be antibody fragments binding to one or more AAV serotypes of the AAV to be isolated. Exemplarily the ligand(s) bind(s) to one or more AAV serotypes selected from the group consisting of AAV1, AAV2, AAV3, AAV4, AAV5, AAV6, AAV7, AAV8 and AAV9 and or any combinations thereof. Exemplarily, the affinity matrix as used in the context of the present invention may be POROS™ CaptureSelect™ AAV Resins: AAV8, AAV9, AAVX. These AAV resins are, e.g., sold by Thermo Fisher Scientific™ under the catalogue nos. A30795 (AAV8), A27359 (AAV9), or A36745 (AAVX). According to the user guide of the POROS™ CaptureSelect™ AAV Resins of Thermo Scientific™, different serotypes/subtypes of AAV (AAV8, AAV9, AAVX) can be purified with high purity using the resin. The POROS™ CaptureSelect™ AAV resin has a crosslinked poly [styrene divinylbenzene] backbone and the particles are surface coated with a cross-linked polyhydroxylated polymer. The coating is further derivatized with an affinity ligand which is a single-domain monospecific antibody fragment. The CaptureSelect™ AAVX affinity resin (Thermo Scientific™) consists of the single-domain heavy chain (VHH) fragment of the heavy chain-only antibodies normally produced by Camelids. This VHH fragment is both highly specific and compact. The AAVX ligand binds serotype-unspecifically. Likewise, the AAV affinity resin AVB Sepharose (as sold, e.g., by Cytiva under the catalogue no. 17372202) could also be used in the context of the present invention. The affinity matrix AVB Sepharose is based on a highly cross-linked agarose matrix, which enables processing of large sample volumes. The affinity ligand is attached to the base matrix via a long, hydrophilic spacer arm. The AAV affinity ligands are Camelidae-derived, single-domain antibody fragments from the immune response of llamas towards the target AAV and recombinantly produced in *S. cerevisiae*. AVB Sepharose binds AAV of subclasses 1, 2, 3, and 5 but not AAV9.

The term "antibody" as used in the context of the present invention refers to any immunoglobulin or fragment thereof, and encompasses any polypeptide comprising an antigen-binding site. The term includes, but is not limited to, polyclonal, monoclonal, monospecific, polyspecific, non-specific, humanized, human, single-chain, chimeric, synthetic, recombinant, hybrid, mutated, grafted, and in vitro generated antibodies. Antibody fragments include Fab, F(ab')2, Fv, scFv, Fd, dAb, which may retain antigen-binding function. Typically, such fragments include an antigen-binding domain. In the context of the present invention, the ligands of the affinity matrix are monospecific antibody fragments binding to the AAV to be isolated.

In the context of the present invention the affinity matrix may be packed into a column. In the context of the present invention the affinity matrix may be packed into column cartridges. For example, column cartridges made of stainless steel could be used in the context of the present invention. Suitable column cartridges are known to the skilled person and are commercially available from, e.g., VDS optilab (VDS optilab, Chromatographietechnik GmbH, Berlin), IDEX Health & Science, LLC (USA) and Repligen Corporation (USA). In the context of the present invention the column cartridge could have a dimension in the range of between 5×2.0 mm and 20×2.0 mm, i.e. 5×2.0 mm, 6×2.0 mm, 7×2.0 mm, 8×2.0 mm, 9×2.0 mm, 10×2.0 mm, 11×2.0 mm, 12×2.0 mm, 13×2.0 mm, 14×2.0 mm, 15×2.0 mm, 16×2.0 mm, 17×2.0 mm, 18×2.0 mm, 19×2.0 mm, and 20×2.0 mm. Exemplarily, in the context of the present invention, a column cartridge with a dimension of 10×2.0 mm as used in the Examples is preferred. Moreover, the column to be used in the context of the present invention may also be defined by their column volume. The column volume of the column to be used in the context of the present invention ranges between 20 and 1000 $mm^3$, i.e. 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 600, 700, 800, 900, and 1000 mm$^3$. Accordingly, in the context of the present invention the column volume ranges between 20 and 1000 mm$^3$, preferably between 20 and 500 mm$^3$, more preferably between 20 and 150 mm$^3$, even more preferably between 25 and 120 mm$^3$, most preferably between 25 and 70 mm$^3$. In the context of the present invention, it is preferred that the column to be used in the context of the present invention has a column volume of between 25 and 70 mm$^3$, i.e. any value between 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, and 70 mm$^3$. Exemplarily, in the appended Examples a column was used with a column volume of 32 mm$^3$. Accordingly, in the context of the present invention, it is preferred that the column volume is below 100 mm$^3$, preferably between 20 and 100 mm$^3$, more preferably between 20 to 95 mm$^3$, most preferably between 25 to 70 mm$^3$. The conversion factor is 0.001 to convert the value mm$^3$ into mL. In other words, the value in mm$^3$ divided by 1000 gives the value in mL. Further, the column of the present invention may be packed with an affinity matrix as described herein, preferably with the CaptureSelect™ AAVX affinity resin (Thermo Scientific™). In the context of the present invention, the skilled person is aware of means and methods how the affinity matrix is packed into a column, preferably a HPLC column. In general, the packing of a column comprises the preparation of a slurry of the resin of the affinity matrix. Subsequently, the slurry is packed into the column, preferably into column cartridges made of stainless steel. In the context of the present invention, the column may be packed as described in the user guide of the affinity matrix POROS™ Capture Select™ AAV Resins (Pub. No. 100038399; Rev. E). Moreover, in the context of the present invention, the packing of the affinity matrix is preferably done as follows: a column, preferably a column cartridge made of stainless steel with a column cartridge dimension of 10×2.0 mm, is closed on one side before the slurry of the affinity material is filled into the open end of the column, e.g., via a pipette. The slurry of the affinity material is filled into the column until the column volume is exceeded. Subsequently, the column stands until some of the liquid evaporated and the slurry of the affinity material is settled into the column. Subsequently, the excess of the slurry is removed before the open end of the column is closed. In the context of the present invention, the column is packed with the affinity matrix so that rebinding effects of the AAV sample with the affinity matrix are avoided. The skilled person is aware of means and methods to determine the rebinding effects of the AAV sample with the affinity matrix. For example, the rebinding effect could be determined by performing two elution steps after the loading of the sample (here: AAV sample) onto the affinity matrix. When a peak could only be detected after the first elution step but not after the second elution step indicates that no rebinding effects occurred. Likewise, the detection of a peak after the first and second elution step indicates that a rebinding effect occurred. Accordingly, in the context of the present invention the column, preferably the column cartridge made of stainless steel, is filled with the affinity matrix, preferably with a slurry of the affinity matrix. In the context of the present invention, it is preferred that the column is packed with/filled with an affinity matrix volume of between 1 μl and 5000 μl (5 ml), preferably between 5 μl and 2500 μl (2.5 ml), more preferably between 50 μl and 2000 μl (2.0 ml), even more preferably between 100 μl and 1500 μl (1.5 ml), most preferably between 100 μl and 150 μl. Exemplarily, in the context of the present invention, a column cartridge with a dimension of 10×2.0 mm may be filled with a slurry volume of the affinity matrix in the range of between 1 μl and 5000 μl (5 ml), preferably between 5 μl and 2500 μl (2.5 ml), more preferably between 50 μl and 2000 μl (2.0 ml), even more preferably between 100 μl and 1500 μl (1.5 ml), most preferably between 100 μl and 150 μl. In the appended Examples a column with a column volume of 32 mm$^3$ was packed with/filled with an affinity matrix volume of 100 to 150 μl. Affinity matrix volume that exceeds the column can be removed.

Accordingly, in the context of the present invention it is preferred that the claimed methods that detect the intrinsic fluorescence of the AAV protein capsids are carried out with a column volume that ranges between 20 and 1000 mm$^3$, preferably between 20 and 500 mm$^3$, more preferably between 20 and 150 mm$^3$, even more preferably between 25 and 120 mm$^3$, most preferably between 25 and 70 mm$^3$.

Further, the operating pressure of the column is above 15 bar, preferably between 15 and 400 bar. The possibility to use operating pressures higher than 100 bar lead to the possibility of using higher flows, resulting in a faster method. This is a big advantage regarding sample throughput. Accordingly, in the context of the present invention, the methods of the present invention may be carried out with an operating pressure of at least 15 bar, preferably between 20 and 400 bar, more preferably between 20 and 300 bar, even more preferred between 20 and 100, most preferably between 20 and 70 bar. Accordingly, in the context of the present invention the operating pressure of the column may be between 15 and 70 bar, i.e. 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, and 70 bar. Furthermore, the skilled person is aware of the fact that the operating pressure is dependent on the used column (volume/length) and may also increase with age. The methods for the determination of the optimal operating pressure lies within the skilled person's common general knowledge.

In the context of the present invention, the affinity matrix is preferably packed into a HPLC column. The term "HPLC" (High-performance liquid chromatography) refers to a form of column chromatography that pumps a sample mixture in a solvent (known as the mobile phase) at high pressure through a column packed with a matrix (stationary phase). In the context of the present invention the HPLC column is packed with the affinity matrix as described herein. The sample, here a sample containing AAV, is carried by mobile phase suitable for binding of the AAV onto the stationary phase. The stationary phase column packed with the affinity matrix interacts with the mobile phase mixture. Although manual injection of samples is encompassed by the present invention, typical HPLC systems in the context of the present invention are fully automated and controlled by a computer. An injector or autosampler, may be employed, connected to an apparatus to house the column hardware, which is further connected to a detector, preferably a fluorescence detection system. In the context of the present invention an autosampler is particularly preferred. Moreover, in the context of the present invention, the detection system may also be a combination of a fluorescence detection system and an UV detector. In the context of the present invention the affinity chromatography HPLC is preferred. Accordingly, in the context of the present invention it is preferred that that the methods of the present invention use HPLC.

According to the present invention, the HPLC methods of the present invention, i.e. the HPLC method for the detection of the capsid titer of (an) AAV(s) and/or the HPLC method for the determination of the content ratio of the AAV capsid(s) comprise(s)/consist(s) the steps of (a) loading of an AAV sample onto an affinity matrix, preferably an affinity chromatography column; and (b) eluting the AAV from the affinity matrix, preferably from an affinity chromatography column. According to the methods of the present invention the AAV sample may be directly loaded onto the affinity matrix, preferably onto an affinity chromatography column. This means that in the context of the present invention the crude cell culture broth may be directly loaded onto the affinity matrix. However, it is preferred in the context of the present invention that the sample is loaded onto the affinity matrix, preferably an affinity chromatography column with a loading buffer. Thus, in the context of the present invention, the HPLC methods of the present invention, i.e. the HPLC method for the detection of the capsid titer of (an) AAV(s) and/or the HPLC method for the determination of the content ratio of the AAV capsid(s) comprise(s)/consist(s) the steps of (a) loading of an AAV sample onto an affinity matrix, preferably an affinity chromatography column with a loading buffer and (b) eluting the AAV from the affinity matrix, preferably from an affinity chromatography column.

In the context of the present invention, the methods, preferably the HPLC methods, further comprise a washing step either before the loading step (a) and/or after the elution step (b). The washing step will be performed with a washing buffer of suitable strength. In the context of the present invention, suitable washing buffers have a composition that allow the preparation of the column for the next sample, meaning it restores suitable binding conditions for the AAV and removes residues of the elution buffer. Exemplarily washing buffers that could be used in the context of the present invention are known to the skilled person and include, e.g., phosphate-buffered saline (PBS), Tris-buffered saline (TBS), or $H_2O$. Washing buffers such as PBS or TBS are commercially available from, e.g., Sigma-Aldrich under the catalogue nos. P3813 (PBS) or PPB023 (TBS). In the context of the present invention, the washing buffers have a pH value of between 6.0 and 8.0, i.e. between 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, or 8.0. Moreover, in the context of the present invention the washing step may also be done after the elution step (b).

According to the methods of the present invention a sample is loaded onto an affinity matrix. In the context of the present invention, the term "sample", without further specification, is intended to generally refer to a specimen which is expected to contain AAV, in particular a specimen from a cell culture producing AAV. In the context of the present invention, the sample may be either a purified or non-purified sample. Accordingly, the methods may further comprise a step of purifying and/or centrifuging the sample before loading onto the affinity matrix. Centrifugation may be beneficial where samples contain macroscopic debris and/or cells. It is, however, preferred in the context of the present invention that the methods do not comprise the step of purifying and/or centrifuging the sample before loading onto the affinity matrix. Accordingly, in the context of the present invention the sample (AAV sample) is a non-purified-sample. As shown in the appended Examples, the claimed methods allow the use of non-purified sample, such as cell culture supernatant. This is advantageous compared to methods such as SEC-MALS because the claimed methods are non-sensitive to the other components that are part of an AAV containing sample, such as cell culture medium and allow a simultaneously clean-up and concentration of the sample; see also Example 10. Accordingly, another advantage over commonly used methods is that the presented methods are non-destructive, i.e., the detected native AAV particles might be collected after detection and then used for further applications. In the context of the present invention, the sample may refer to the crude cell culture broth, cell lysate as well as filtrates and/or purified version thereof. The sample may also be formulated rAAVs, e.g. in form of a pharmaceutical composition, which can advantageously be measured just prior to application in order to assure that the virus titer is correct. In the context of the present invention, means and methods for the filtration and/or purification of AAV samples are well known in the art; see, e.g., Adams et al., Biotechnology and Bioengineering (2020), Vol. 117, Issue 10, pp. 3199-3211.

Accordingly, in the context of the present invention, the AAV sample may contain a heterogenous mixture of empty, partially-filled and full capsids. Further the heterogenous AAV sample in the context of the present invention may contain aggregates of the capsids. The AAV sample may also be homogeneous, e.g. be substantially full capsids or substantially empty capsids or substantially partially-filled capsids. Moreover, in the context of the present invention the AAV sample may also be processed to ensure that, e.g., a concentrated AAV sample is used that may, e.g., only contain full or empty capsids. The skilled person is aware of means and methods to process the AAV sample. Exemplarily, a chromatographic separation could be used. The term "full capsid" in the context of the present invention refers to an AAV capsid that contains the protein capsids and the complete DNA of interest, e.g., genome carrying the full transgene. The term "full capsid" also refers to an AAV capsid that may contain more than 1 complete genomes carrying the full transgene. The content of the "full capsids" at the end of the production process (i.e. the time of harvest) is commonly less than 30%. The term "partially-filled capsid" refers in the context of the present invention to AAV capsids where the capsid contains, e.g., fragments of DNA or non-transgene DNA. The content of "partially-filled capsids" at the end of the production process (i.e. the time of harvest) is commonly less than 10%. The "empty capsid" in the context of the present invention refers to capsids that do not contain DNA. The content of the "empty capsids" at the end of the production process (i.e. the time of harvest) is commonly less than 70%. The term "aggregate(s)" refers in the context of the present invention to dimeric or trimeric capsids. The content of the "aggregates" at the end of the production process (i.e. the time of harvest) is commonly more than 2%. Notably, it can be assumed that AAV aggregation increases over time, when the samples are not frozen, but the quantification of those samples was still satisfactory.

Moreover, in the context of the present invention, the AAV sample may also contain impurities or contaminants. The term "impurity" or "contaminant" refers to any foreign molecule, such as DNA, RNA, one or more host cell proteins (HCPs), endotoxins, lipids and one or more additives which may be present in a sample containing the AAV capsids. An impurity may be soluble or insoluble in nature. Insoluble impurities include any undesirable or objectionable entity present in a sample containing AAV particles, where the entity is a suspended particle or a solid. Exemplary insoluble impurities include without limitation, whole cells, cell fragments and cell debris. Soluble impurities include any undesirable or objectionable entity present in a sample containing AAV particles where the entity is not an insoluble impurity. Exemplary soluble impurities include without limitation, host cell proteins, DNA, RNA, lipids viruses, endotoxins, and cell culture media components. As shown in Example 5, the HCPs are not bound by the affinity matrix, which renders it plausible that the claimed methods separate impurities such as HCP from the AAV sample (see also results in FIG. 5).

According to the methods of the present invention, the sample containing AAV (AAV sample) is loaded onto an affinity matrix. The term "load" means in the context of the present invention that the sample is brought into contact with the affinity matrix. In the context of the present invention, the sample may be either loaded onto the affinity matrix by using, e.g., an autosampler or via a channel on the pump. In the context of the present invention, the loading of the sample via an autosampler is preferred. The sample volume to be loaded can vary, depending on the concentration of the AAV concentration in the sample. In the context of the present invention, the sample containing AAV (AAV sample) is loaded onto the affinity matrix with a volume of less than 1500 µl (1.5 ml), preferably equal to or less than 1300 µl, more preferably equal to or less than 1200 µl (1.2 ml), even more preferably equal to or less than 1100 µl (1.1 ml), or most preferably equal to or less than 1000 µl (1.0 ml). Exemplarily in the context of the present invention the volume ranges between 1 µl and 1500 µl (1.5 ml), more preferably between 5 µl and 1500 µl (1.5 ml), even more preferably between 50 µl and 1500 µl (1.5 ml), most preferably between 100 µl and 1000 µl. Accordingly, in the context of the present invention the loaded sample volume ranges between 1 µl and 1500 µl, i.e. any volume between 1 µl, 2 µl, 3 µl, 4 µl, 5 µl, 6 µl, 7 µl, 8 µl, 9 µl, 10 µl, 11 µl, 12 µl, 13 µl, 14 µl, 15 µl, 16 µl, 17 µl, 18 µl, 19 µl, 20 µl, 21 µl, 22 µl, 23 µl, 24 µl, 25 µl, 26 µl, 27 µl, 28 µl, 29 µl, 30 µl, 31 µl, 32 µl, 33 µl, 34 µl, 35 µl, 36 µl, 37 µl, 38 µl, 39 µl, 40 µl, 41 µl, 42 µl, 43 µl, 44 µl, 45 µl, 46 µl, 47 µl, 48 µl, 49 µl, 50 µl, 60 µl, 61 µl, 62 µl, 63 µl, 64 µl, 65 µl, 66 µl, 67 µl, 68 µl, 69 µl, 70 µl, 71 µl, 72 µl, 73 µl, 74 µl, 75 µl, 76 µl, 77 µl, 78 µl, 79 µl, 80 µl, 81 µl, 82 µl, 83 µl, 84 µl, 85 µl, 86 µl, 87 µl, 88 µl, 89 µl, 90 µl, 91 µl, 92 µl, 93 µl, 94 µl, 95 µl, 96 µl, 97 µl, 98 µl, 99 µl, 100 µl, 200 µl, 300 µl, 400 µl, 500 µl, 600 µl, 700 µl, 800 µl, 900 µl, 1000 µl, 1100 µl, 1200 µl, 1300 µl, 1400 µl and 1500 µl. In the context of the present invention, multiple loading steps are also possible. Multiple loading steps may be necessary, if, e.g., the sample which is loaded onto the affinity matrix, preferably the sample that is loaded onto the affinity chromatography matrix, is diluted. Multiple loading steps ensure that enough sample for the subsequent detection is loaded onto the affinity matrix, preferably the affinity chromatography matrix. In the context of the present invention a multiple loading means that the AAV sample is loaded onto one affinity matrix with more than one sample injection, e.g. by an autosampler, preferably a HPLC autosampler. Multiple loading steps broaden the application of the present method, since the total sample volume may increase from 1 µl to several ml.

In the context of the present invention, a sample, preferably an AAV sample, with a volume of less than 1500 µl (1.5 ml), preferably equal to or less than 1300 µl, more preferably equal to or less than 1200 µl (1.2 ml), even more preferably equal to or less than 1100 µl (1.1 ml), or most preferably equal to or less than 1000 µl (1.0 ml) is loaded onto an column that is filled with a slurry volume of the affinity matrix in the range of between 1 µl and 5000 µl (5 ml), preferably between 5 µl and 2500 µl (2.5 ml), more preferably between 50 µl and 2000 µl (2.0 ml), even more preferably between 100 µl and 1500 µl (1.5 ml), most preferably between 100 µl and 150 µl.

The loading time in the methods of the present invention depend on the system volume and the flow rate. In principle, it is important that the AAV sample has sufficient time to be in contact with the affinity matrix, preferably flow over the HPLC column packed with the affinity matrix. This means that with a sample volume of 0.5 ml, it must be considered that the sample flows through the entire volume of the chromatography system plus column before the initiation of the elution step. In concrete terms, with the set-up as explained in the appended Examples, the total volume would be 2.0 ml for a sample volume of 0.5 ml. Consequently, this also means that the loading time of an AAV sample (0.5 ml) with the chromatography set-up as reported in the appended Examples takes 5 minutes. Accordingly, in the context of the present invention, the sample containing AAV (AAV sample) may be loaded onto the affinity matrix with a flow rate of about 0.4 to 0.7 ml/min (i.e. 0.4, 0.5, 0.6, or 0.7 ml/min) for about 5 to 10, preferably 6 to 9 minutes. As the loading time and the volume depend on the chromatography system, the loading time could be reduced. Thus, in the context of the present invention the chromatography set-up can be modified (e.g., by the use of a smaller column, higher flow rate, etc.) so that the loading time will be reduced from 5 minutes to approximately 1 to 2 minutes. Higher flow rates are also desired in order to achieve shorter times and higher sample throughout. In the context of the present invention it is intended that the flow rate could be increased from about 0.5 to 0.6 ml/min up to 1 to 1.5 ml/ml. At higher flow rates the loading time can be reduced, resulting in (a) faster method(s).

In the context of the present invention, it is preferred that a column cartridge with a dimension of 10×2.0 mm is filled with an affinity matrix as described herein. Further, it is preferred that a column cartridge made of stainless steel is used. Accordingly, in the context of the present invention it is preferred that a stainless steel column with a dimension of 10×2.0 mm is filled with an affinity matrix as described herein. Further, it is particularly preferred that the sample containing AAV (AAV sample) is loaded onto the stainless steel column (10×2.0 mm) with a flow rate of about 0.4 to 0.7 ml/min (i.e. 0.4, 0.5, 0.6, or 0.7 ml/min). Most preferably, the sample containing AAV (AAV sample) is loaded via injection by an autosampler onto the stainless steel column (10×2.0 mm) with a flow rate of about 0.4 to 0.7 ml/min (i.e. 0.4, 0.5, 0.6, or 0.7 ml/min).

According to the methods of the present invention the AAV sample may be directly loaded onto the affinity matrix, preferably an affinity chromatography column. This means that in the context of the present invention the crude cell culture broth or cell culture supernatant may be directly loaded onto the affinity matrix. In the context of the present invention, the AAV sample may also be loaded onto the affinity matrix with a loading buffer.

The "loading buffer" in the context of the present invention may be any buffer suitable to load the sample containing AAV capsids onto the affinity matrix. In the context of the present invention, the loading buffer is a buffer characterized by a neutral pH. Accordingly, in the context of the present invention the loading buffer is a buffer having a pH value between about 6.0 and about 8.0, i.e. 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, or 8.0. Exemplarily, the loading buffer in the context of the present invention may be a phosphate-buffered-saline (PBS) buffer (pH 7.0), Tris-buffered saline (TBS) buffer, MOPS (3-(N-morpholino) propanesulfonic acid) buffer, or HEPES (4-(2-hydroxyethyl)-1-piperazineethanesulfonic acid) buffer. In the context of the present invention, a PBS, TBS, MOPS or HEPES buffer is used with a pH value between about 6.0 and about 8.0. Loading buffers such as PBS or TBS are commercially available from, e.g., Sigma-Aldrich under the catalogue nos. P3813 (PBS) or PPB023 (TBS). The skilled person is aware how to measure the pH in a loading buffer via standard methods. For example, the pH could be measured via a pH electrode or via a blood gas analyzer. The term "about" in the context of the pH value means means 10 percent more or 10 percent less than the denoted value.

As explained above, the present methods are based on the use of an affinity matrix. Further, as has been explained an affinity matrix can be, e.g., POROS™ CaptureSelect™ AAV Resins (Thermo Fisher Scientific™) or the AAV resin Capto AVB (Cytiva). Before loading the affinity matrix with the sample containing AAV capsids (AAV sample), it may be necessary to adjust parameters such as pH, ionic strength, and temperature and in some instances the addition of substances of different kinds. Thus, it is an optional step to perform an equilibration of the affinity matrix by washing it with a solution (e.g., a buffer for adjusting pH, ionic strength, etc., or for the introduction of a detergent) bringing the affinity matrix in a state, free of the buffer which may be present, e.g. residual elution buffer or buffer the affinity matrix was stored in. In the context of the present invention, the affinity matrix is equilibrated with the loading buffer. In the context of the present invention, the affinity matrix is equilibrated with the loading buffer for at least 5 minutes.

In the context of the present invention the AAV capsid(s) contained in the sample is (are) preferably eluted from the affinity matrix by the use of an elution buffer. The term "elution buffer" refers in the context of the present invention to an acidic buffer. In other words, the elution of the AAV bound on the affinity matrix occurs through a pH shift from neutral pH to acidic pH. As explained above, a buffer with a neutral pH has a pH value of between about 6.5 and about 7.5. In the context of the present invention, the acidic buffer has a pH of less than or equal to 4.0, preferably less than or equal to 3.0, i.e. 3.0, 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, or 1.0. Different salts, amino acids or other ingredients may be part of the elution buffer. Thus, the components of the elution buffer may be adjusted according to the knowledge of the skilled person. Exemplarily, in the context of the present invention (and as shown in the appended Examples) the elution buffer may contain glycine, arginine and sodium chloride (NaCl), at pH 2.3. In the context of the present invention the elution buffer may contain glycine at a concentration of between 10 and 100 mM, i.e. 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mM. Likewise, the elution buffer may contain arginine at a concentration of between 25 and 250 mM, i.e. 25, 26, 27, 28, 29, 30, 31, 32, 33, 34, 35, 36, 37, 38, 39, 40, 41, 42, 43, 44, 45, 46, 47, 48, 49, 50, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, or 250 mM. Likewise, in the context of the present invention, the elution buffer may also contain 200 mM sodium chloride (NaCl). In the appended Examples, elution buffers having either 10 mm glycine, 100 mM glycine, 25 mM arginine, 250 mM arginine, or 200 mM NaCl were experimentally tested and each of these tested ingredients worked equally well. As the binding/elution behavior of the AAV sample on the affinity matrix may differ, the best elution could be determined experimentally by the skilled person as described in the user guide of the affinity matrix POROS™ Catpure Select™ AAV Resins (Pub. No. 100038399; Rev. E): · Start with 50-100 mM citric acid pH 3.0. · To elute most target molecules (here: AAVs), reduce the pH to the range of pH 2 to 3. · Other elution buffer components that can be used include phosphate, hydrochloric acid, glycine, acetate, or other components that buffer well at low pH. Other additives such as equal or less than 2 M $MgCl_2$ (pH 7) or equal or less than 50% propylene glycol may be useful. Combinations of these components can be used to optimize elution conditions. · Use an elution buffer strength greater than the equilibration buffer strength to ensure a good pH transition. · Use a step elution to obtain a concentrated elution fraction, then a gradient if additional separation for very similar product impurities is needed. · Do not underload the column. A load significantly below the maximum binding capacity can hamper efficient release due to rebinding events during elution causing poor recovery. · Immediately neutralize the eluted pool to prevent denaturation of some molecules at low pH. When selecting buffer systems, consider molecule stability, binding optimization for the next step, and the ability of the buffer to control pH in the desired operating range. Accordingly, the skilled person is aware to experimentally determine the elution conditions. Moreover, the skilled person is aware how to measure the pH in an elution buffer via standard methods. For example, the pH could be measured via a pH electrode or via a blood gas analyzer. The term "about" in the context of the pH value means 10 percent more or 10 percent less than the denoted value.

The elution in the methods of the present invention is based on the principle that the binding between the AAV and the affinity matrix breaks after the pH shift from a neutral pH to an acidic pH. In the context of the present invention, the elution may require a complete change of the loading buffer to the elution buffer, i.e. 100% of the loading buffer is replaced by 100% of the elution buffer. In the context of the present invention, the elution may also be performed by a gradient, which means that not 100% of the loading buffer is replaced by 100% of the elution buffer. Accordingly, in the context of the present invention the elution is performed by a gradient if, e.g., 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, or 70% of the loading buffer is replaced by the elution buffer. The elution step may also be done in such way that the loaded affinity matrix is contacted with an elution buffer, preferably for 1 to 2 minutes, and subsequently contacted with a storage buffer, thereby eluting the AAV from the affinity matrix. The storage buffer allows for providing the AAVs a surrounding buffer that improves their stability compared to the elution buffer. In the context of the present invention the "storage buffer" may have the same composition and pH as the loading buffer or may have a different composition and pH. Exemplarily, in the context of the present invention, the storage buffer may be aqueous, e.g., $H_2O$, phosphate-buffered saline (PBS), or Tris-buffered saline (TBS). Buffers such as PBS or TBS are commercially available from, e.g., Sigma-Aldrich under the catalogue nos. P3813 (PBS) or PPB023 (TBS). In this elution step, the affinity matrix will be contacted with the storage buffer for at least 1 minute, preferably between 1 to 10 minutes. Accordingly, the methods of the present invention may comprise the following steps: (a) loading a sample (AAV sample) onto an affinity matrix, preferably a HPLC affinity chromatography; (b) contacting the affinity matrix, preferably a HPLC affinity chromatography, with an elution buffer, preferably for 1 to 2 minutes; (c) contacting the affinity matrix with a storage buffer thereby recovering the affinity matrix. Such elution procedure may be advantageous because the sample may be recovered in buffer (storage buffer, e.g. loading buffer) with a neutral pH (i.e. a pH which does not harm the AAV). Furthermore, when the storage buffer has the same composition as the loading buffer, the column is already equilibrated with the loading buffer and can be directly used again. As explained above, in the context of the present invention, multiple loading steps are also possible. Multiple loading steps may be necessary, if e.g., the sample which is loaded onto the affinity matrix, preferably the sample that is loaded onto the affinity chromatography matrix, is diluted. Moreover, in the context of the present invention, the loading of the AAV sample onto the affinity matrix and the elution of the affinity matrix may be performed by either one device method or a plurality, e.g. two, device methods.

The affinity matrix may optionally be cleaned and regenerated after elution of the AAV. This procedure is typically performed regularly to minimize the building up of impurities on the surface of the solid phase of the affinity matrix and/or to sterilize the affinity matrix to avoid contamination of the eluted AAV.

In the context of the present invention, the term "AAV" is an abbreviation for adeno-associated virus and may be used to refer to the virus itself or modifications, derivatives, or pseudotypes thereof. In the context of the present invention the term "AAV" includes the AAV type 1 (AAV1), AAV type 2 (AAV2), AAV type 3 (AAV3), AAV type 4 (AAV4), AAV type 5 (AAV5), AAV type 6 (AAV6), AAV type 7 (AAV7), AAV type 8 (AAV8), AAV type 9 (AAV9), avian AAV, bovine AAV, canine AAV, equine AAV, primate AAV, non-primate AAV, and ovine AAV, and modifications, derivatives, or pseudotypes thereof. "Primate AAV" refers to AAV that infect primates, "non-primate AAV" refers to AAV that infect non-primate mammals, "bovine AAV" refers to AAV that infect bovine mammals, etc.

In the context of the present invention the AAV may also refer to a recombinant adeno-associated virus (rAAV). The term "recombinant", as applied to an AAV means that the AAV is the product of one or more procedures that result in an rAAV that is distinct from an AAV in nature. A "rAAV" refers to a viral particle composed of at least one AAV capsid protein and a polynucleotide rAAV vector comprising a heterologous polynucleotide (i.e. a polynucleotide other than a wild-type AAV genome such as a transgene to be delivered to a mammalian cell). The rAAV particle may be of any AAV serotype, including any modification, derivative or pseudotype (e.g., AAV1, AAV2, AAV3, AAV4, AAV5, AAV6, AAV7, AAV8, AAV9, or AAV10, or derivatives/modifications/pseudotypes thereof). Such AAV serotypes and derivatives/modifications/pseudotypes, and methods of producing such serotypes/derivatives/modifications/pseudotypes are known in the art (see, e.g., Asokan et al, Mol. Ther. (2012), Vol. 20 (4), pp. 699-708).

In the context of the present invention the capsid titer in the eluate is detected by a fluorescence detection system. Accordingly, the present invention relates to a method for the detection of the capsid titer, wherein the method comprises/consists the steps of (a) loading of an AAV sample onto an affinity matrix, preferably an affinity chromatography column, with a loading buffer; (b) eluting the AAV from the affinity matrix, preferably from an affinity chromatography column; and (c) detecting the AAV capsid titer in the eluate with a fluorescence detection system. In the context of the present invention, the AAV capsid titer is detected by using an HPLC system with a fluorescence detection system. Fluorescence detection system refers in the context of the present invention to a spectroscopy method in which the AAVs, preferably the AAV capsids, absorb light to reach a high-energy level and then emits light to return to its original level. The AAVs, preferably the AAV capsids, have wavelengths of light that they absorb (excitation wavelengths) and emit (emission wavelengths). In the context of the present, the AAV capsids are detected with a fluorescence detection system at an excitation wavelength of between 200 and 290 nm, i.e. 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289 or 290 nm and at an emission wavelength of between 330 and 350, preferably between 340 and 350, i.e. 340, 341, 342, 343, 344, 345, 346, 347, 348, 349, or 350 nm. Exemplarily, in the appended Examples, the AAV capsids were detected with a fluorescence detection system at an excitation wavelength of 214 nm, preferably 280 nm, and at an emission wavelength of 350 nm. By using an excitation wavelength of between 200 nm and 290 nm, preferably 280 nm, and an emission wavelength in range between 320 and 350 nm, preferably 350 nm, the skilled person knows that the intrinsic fluorescence of the aromatic amino acids in the AAV capsids proteins is measured in the methods of the present invention.

Moreover, in the context of the present invention, the method for the detection of the capsid titer of an AAV may further comprise the step of quantifying the eluate comprising the AAV by an UV spectrophotometry method. Accordingly, in the context of the present invention, the method for the detection of the capsid titer of an adeno-associated virus (AAV) comprises the following steps: (a) loading an AAV sample onto an affinity matrix with a loading buffer; (b) eluting the AAV from the affinity matrix; (c) detecting the AAV capsid titer in the eluate with a fluorescence detection system; and (d) quantifying the eluate comprising the AAV by an UV spectrophotometry method. In the context of the present invention the quantification of the eluate comprises the determination of the AAV in the eluate at 260 nm. The UV absorbance measurement at 260 nm, preferably in a HPLC set-up, may be used in the context of the present invention to measure the genomic DNA content of the AAV capsids. Thus, the methods of the present invention allow the simultaneous measurement of the genomic titer (DNA) via the UV absorbance measurement and capsid titer via the fluorescence detection system.

Further, the simultaneous detection of the AAV capsid titer (via the fluorescence detection system) and the genomic titer (via the UV spectrophotometry method) allows the determination of the ratio of full and empty capsids of an AAV. Accordingly, the present invention also relates to a method for the determination of the ratio of full and empty capsids of an AAV, wherein the method comprises the following steps: (a) loading an AAV sample onto an affinity matrix with a loading buffer; (b) eluting the AAV from the affinity matrix; and (c) detecting the AAV in the eluate with a fluorescence detection system and with an UV spectrophotometry method thereby determining the ratio of full and empty capsids of the AAV.

For the quantification of either the capsid titer or the genome (DNA) content, an external calibration curve may be used in the context of the present invention. In the context of the present invention, the amount of external calibration samples, i.e. AAV samples with a defined concentration of either the capsid (protein) or the genome (DNA) is not limited. In the context of the present invention it is preferred to use 3 to 5 calibration samples. The calibration samples are created by the measurement of known AAV samples with different amounts of AAV. In the context of the present invention, any amount of AAV could be taken as calibration sample as long as the sample amount lies between the minimum and maximum loading capacity of the affinity matrix. Exemplarily, the calibration could be done with AAV samples that contain between 5E+11 to 9E+12 capsid particles (cps) per ml. In the context of the present invention, calibration samples may be either from the same AAV serotype or from different AAV serotypes. As shown in the appended Examples, calibration samples of AAV8 could also be used for AAV5 samples, implying that it is not necessarily serotype specific. Accordingly, the present invention also relates to a method for the quantification of the capsid titer of an adeno-associated virus (AAV), wherein the method comprises the following steps:
 (a) loading an AAV sample onto an affinity matrix;
 (b) eluting the AAV from the affinity matrix;
 (c) detecting the AAV capsid titer in the eluate with a fluorescence detection system; and
 (d) quantifying the capsid titer by using a calibration sample.

Likewise, in the context of the present invention, the quantification of the AAV in the AAV samples may be done in an absolute manner (without a calibration sample) and either by the determination of the peak area and/or of the maximum height of the determined peak. The skilled person is aware of software that can be used for the quantification via the peak area and/or of the maximum height of the determined peak. For example, in the presented Examples the Agilent Chemstation Software was used.

BRIEF DESCRIPTION OF THE DRAWING FIGURES

The Figures show:
FIG. 1: Example chromatogram for the affinity based detection of AAV (here: AAV8). Here 2.05E+12 capsids from a cell culture sample were directly applied to the method. After elution of the AAV, the sample was detected via fluorescence with excitation at 280 nm and emission at 350 nm. A clear and sharp peak representing the AAV could be detected.

Figure 2:
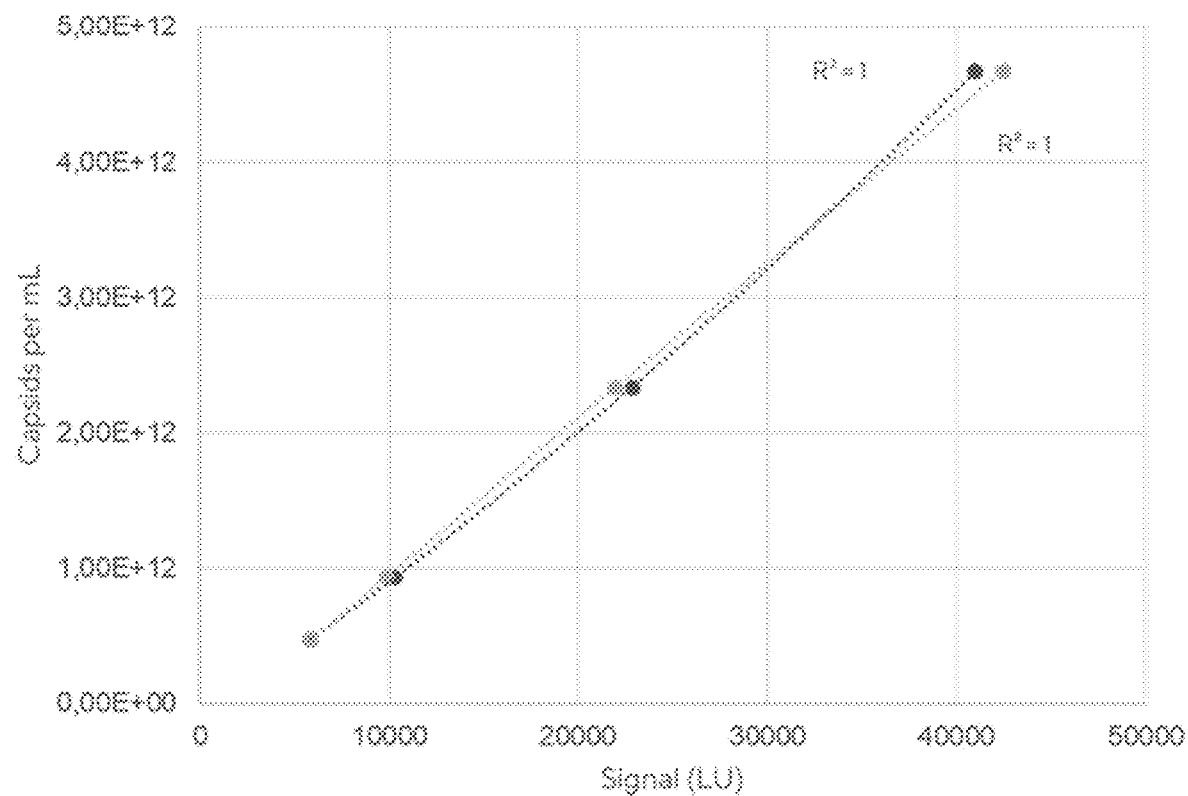

FIG. 2: Correlation of AAV capsid concentration (here: AAV8) as measured by fluorescence detection (FLD). Four different concentrations of AAV were applied to the described method and the previously known concentration was correlated with the detected peak area. The experiment was repeated with the same AAV8 concentrations on a different day and using a different column. Both correlations show a correlation factor of 1. This indicates the methods suitability for quantifying AAV capsids.

FIG. 3: Determination of the correlation of variation (CV) for 5 aliquots of the same AAV8 sample. Three aliquots were measured on one day, while two further aliquots were measured on a different day. Displayed are the absolute measurements, their deviation as compared to an ELISA measurement of the same sample and the CVs of the sample aliquots per day and in total.

FIG. 4: AAV from 3 mL culture (here: AAV8 culture) were collected in 1.5 mL and the capsid concentration of the eluate as well as the concentration of the initial culture were determined to show that the integrity of the AAV remains intact.

Figure 5:
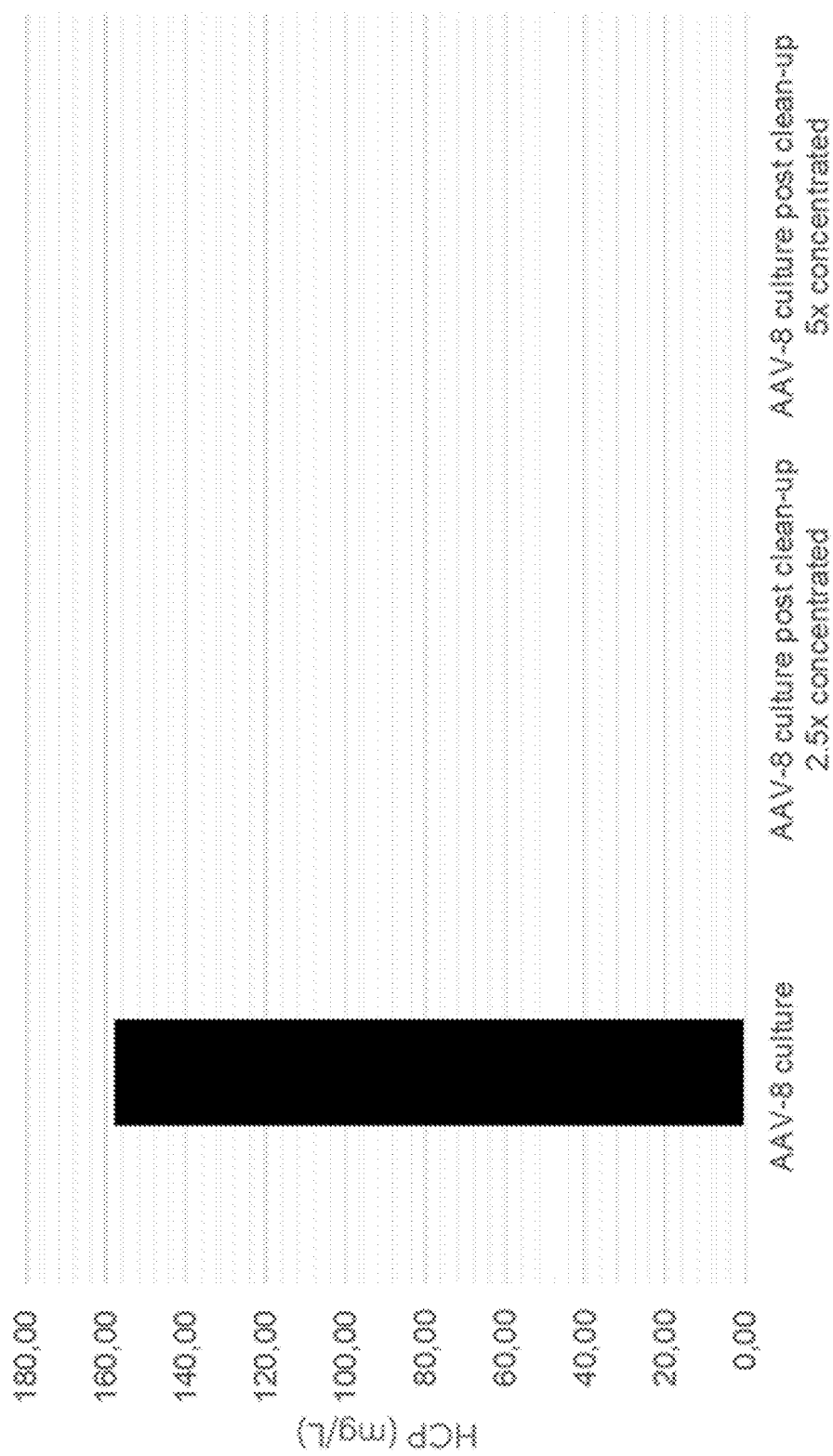

FIG. 5: Determination of host cell proteins (HCP) via ELISA. The described method was used to concentrate an AAV8 containing culture. One sample was 2.5× concentrated and the other sample 5×. Both were compared to the initial culture to show the effectiveness of separating the AAV from the culture.

FIG. 6: To show the serotype independence of the described method, a cell culture sample containing AAV5 was calibrated AAV8. Displayed are the total concentration of AAV5 capsids per mL, the deviation to the measured AAV5 concentration as per ELISA and the CV.

Figure 7:
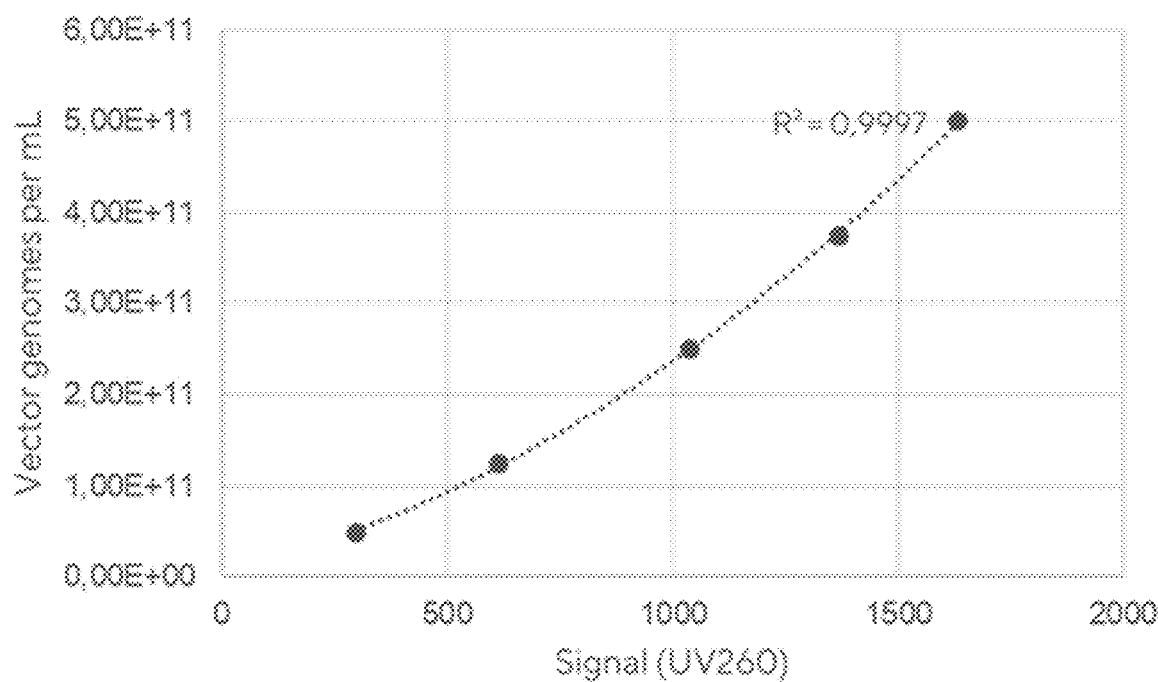

FIG. 7: Correlation of AAV vector genome (VG) concentration (here: AAV8) as measured by UV detection. Five different concentrations of AAV were applied to the described method and the previously known concentration was correlated with the detected peak area. The method shows a correlation factor of above 0.99. This indicates the methods suitability for quantifying AAV vector genomes.

FIG. 8: Detection of empty/full AAV particles. The method can provide results for the capsid titer (fluorescence) and genomic titer (UV). Their correlation allows the calculation of the empty to full AAV particle ratio, a critical quality parameter.

FIG. 9: Different samples were used for the presented affinity HPLC quantification and compared to ELISA results, to show that the method does not depend on a certain type of sample. Displayed are an AAV8 sample gained by ultrafiltration, an AAV 8 sample from cell culture supernatant and an AAV5 sample from cell culture supernatant.

FIG. 10: Simultaneous detection of AAV capsids using fluorescence (280 nm→350 nm) and UV (280 nm) shows a stronger signal for the same amount of AAV capsid when fluorescence is used.

FIG. 11: Comparison of developed method compared to prior art methods using cell culture samples (table A referring to "Crude extract") and purified samples (table B referring to "Purified extract").

FIG. 12: Chromatograms of an AAV8 sample that was cleaned applying the method according to the present invention measured by SEC with MALS (grey) and UV (black) detection. A: Whole chromatogram. B: Zoom on AAV. Scaling is relative, the highest peak in per trace (MALS and UV) in the focused area is displayed as 1.0.

FIG. 13: Chromatograms of an AAV8 sample that was filtered measured by SEC with MALS (grey) and UV (black) detection. A: Whole chromatogram. B: Zoom on AAV.

Scaling is relative, the highest peak in per trace (MALS and UV) in the focused area is displayed as 1.0.

EXAMPLES

The following Examples were carried out with the following experimental set up: Agilent 1260 Quad Pump (G1311B), Agilent 1260 Autosampler (G1329B), Agilent 1290 Column compartment (G1316C), Agilent 1260 Infinity Variable Wavelength Detector (G1314F), Agilent 1260 Infinity Fluorescence Detector (G1321B) and Agilent 1260 Fraction collector (G5654A) (Agilent Technologies, U.S.A.).

Example 1: "Chromatograms"

Experimental details: Supernatant of an AAV8 containing cell culture sample (0.5 ml) was loaded onto the affinity column (column cartridge dimension=10×2.0 mm). Loading was achieved by injecting the sample into the HPLC System using the Multidraw option installed in the autosampler. Phosphate-buffered-saline (PBS) with a pH at 7.2 was used as mobile phase during column loading. Elution happened with a buffer containing glycine, arginine and sodium chloride at pH 2.3. Flow was set to 0.6 mL throughout the whole experiment. Peak detection was carried out with a fluorescence detector (FLD) at 280 nm excitation and 350 nm emission.

Results: A clear and sharp peak could be detected; see FIG. 1. It is well distinguishable, since no background was measured. During similar experiments it was seen that the peak area (as well as the peak height) correlates to the AAV concentration.

Interpretation: The column works as intended: Affinity chromatography should lead to one clear peak without interfering substances. The integrity of the column can be tested when repeating experiments result in the same peak shape, eluting at the same time. Differences occur when the method is adapted to a faster or slower flow-through. Only the peak area and height should be variable within one method setup. Having tested the consistency of the method, calibration tests as disclosed in Example 2 followed.

Example 2: "Calibration"

Experimental details: 4 different amounts of AAV8 (i.e., 4.67E+11; 9.35E+11; 2.34E+12; 4.7E+12 capsids/ml) were used for the method described above. Different volumes of sample (0.1; 0.2; 0.5; 1.0 ml) were injected. The peak area (peak height may be used as well) was correlated to the AAV amount per sample volume. The amount of AAV was determined by PROGEN's ELISA Kits (Cat. No. PRAAV8XP (PROGEN Biotechnik GmbH, Germany) according to the manufacturer's manual. The detection was carried out via a Multimode Plate Reader according to the manufacturer's manual.

Results: A clear, reproducible regression could be achieved in independent trials with regression coefficients of 1; see Figure. 2.

Interpretation: These results show the clear correlation of AAV amount and peak size, making it a feasible method for AAV quantification.

Example 3: "Quantification"

Experimental details: A calibration, like described in Example 2 was used to quantify a different AAV8 containing sample. In order to get results in accuracy and (intermediate) precision the aliquots were measured as two sets. 3 samples were measured in one sequence, 2 samples were measured on a different day. Accuracy was observed as comparison to ELISA values, precision was observed as variation of the results within the 5 samples.

Results: All 5 samples show results between 4.33E+12 and 4.58E+12 capsids per ml, which equals to an overall precision with a coefficient of variation of 2.2. The accuracy as compared to ELISA values of the same sample is very promising with values of 1.9% to 7.2% deviations. The results are shown in Figure. 3.

Interpretation: The results are consistent throughout several measurements and independent of time (and column batch). The accuracy shows good results, indicating that the method can be used instead of other quantification processes. Furthermore, the coefficient of variation is better than the one of ELISAs (less than 10%; see Gimpel et al., Molecular Therapy: Methods & Clinical Development (2021), Vol. 20, pp. 740-754), indicating advantages as compared to ELISA. No clean-up was used and therefore sample handling is easy and practical, which further increases the value of the described method, in contrast to methods like ELISA. Quantification was successfully tested with AAV serotypes 2 (AAV2), 5 (AAV5) and 8 (AAV8), indicating an overall non serotype specific and robust measurement.

Example 4: "Non-Destructive Method"

Experimental details: Since the method can not only be used for quantification, but in parallel for small scale purifications and concentrations (AAV are not modified throughout the whole method), it was tested whether the AAV are destroyed during processing. Therefore, 3 mL of AAV8 cell culture were applied to the method and the eluted peak was collected. The collected sample and the original sample were used for ELISA measurements.

Results: The results are 1.2E+13 capsids in 1.5 mL for the collected sample and 1.4E+13 capsids per 3 mL for the initial culture. The recovery is 86%, while the volume is 50%. The results are shown in FIG. 4.

Interpretation: The results indicate that the AAV are still intact and that next to a clean-up a concentration can be achieved. Although, it is not surprising that the total number of capsids might differ slightly, the coefficient of variation of the ELISA needs to be taken into account.

Example 5: "Product Cleaning"

Experimental details: Host cell proteins (HCP) can be used as marker for sample clean-up. The original culture shows these proteins, as they belong to the used host cell. During cleaning, these proteins should decrease, while the product is not affected. Host cell proteins can be measured with dedicated ELISAs. Two cleaned samples were measured against the original culture.

Results: The culture showed 157.82 mg of HCP per liter. In contrast both cleaned samples showed only 0.08 g of HCP per liter, for both a 2.5× and a 5× concentrated sample. The results are shown in FIG. 5.

Interpretation: The developed method successfully separates the original culture from the desired AAV target.

Example 6: "Serotype Independence"

Experimental details: AAV5 samples were taken and applied to the column. Two samples were measured on different days in order to show the robustness. The method was not changed to the previously described method.

Results: The samples showed titers of 7.02E+11 and 6.80E+11 which deviates 3.9% and 0.6%, respectively, to the AAV5 specific ELISA measurements (Cat. No. PRAAV5XP (PROGEN Biotechnik GmbH, Germany). The coefficient of variation is 1.6. The results are shown in FIG. 6.

Interpretation: Not only for AAV8, but also for AAV5 good accuracy and precision values were obtained. This indicates a general ability of quantification throughout different serotypes.

Example 7: "DNA Detection for Genomic Titer Determination"

Experimental details: A UV detector (Agilent 1260 Infinity Variable Wavelength Detector (G1314F)) was added to the experimental setup and it was set to detection at 260 nm. For the sake of clarification, the protein and DNA are measured in one peak and the ratio of the empty vs. full AAV particles is determined therefrom. 5 different known amounts of AAV8 containing samples were used to correlate the peak size to the genomic titer. These samples were used as calibration. The genomic titer was determined by ddPCR. Then, an independent sample was used to determine its genomic titer.

Results: The correlation of the calibration samples was at 0.9997 and therefore a clear correlation of peak size to genomic titer can be drawn. The genomic titer was measured at 5.88E+10 vector genomes, which is in accordance to a control ddPCR. Since both detectors are in line, the fluorescence was measured too. Therefore, the genomic titer and the capsid titer were detected in one run. The results are shown in FIGS. 7 and 8.

Interpretation: The ratio of empty vs. full AAV particles is a very important feature in AAV samples. The simultaneous measurement of genomic titer and capsid titer enables a powerful combination of results, without the need of separate measurements like PCR and ELISA. This is a huge advantage of the proposed method.

Example 8: "Sample Independence"

Experimental details: To show that the method not only works for cell culture supernatant, but independently from the matrix, culture supernatant was compared to a sample generated by ultrafiltration. Ultrafiltration is a concentration step for bigger molecules. Small molecules are washed out with 90% of the culture, bigger particles and proteins are concentrated in 10% of the original volume. Therefore, ultrafiltration samples show a matrix that is very much different from culture supernatants.

Results: Both the results derived from supernatant and after ultrafiltration are in close proximity to the results obtained by ELISA measurements. The results are shown in FIG. 9.

Interpretation: These results are a strong hint towards the methods robustness. The ability to produce good results for any matrix, such as filtrates, concentrates, lysates, cleaned or processed samples, makes the method interesting for a lot of applications resulting in a variety of samples.

Example 9: "Capsid Detection Fluorescence Detector (FLD) Vs. UV Detection (UV)"

Experimental details: 2.05E+12 AAV8 capsids (contained in 1 ml supernatant of an AAV8 containing cell culture) were loaded onto the affinity column (dimension 10×2 mm). Loading was achieved by injecting the sample into the HPLC System using the Multidraw option installed in the autosampler. Phosphate-buffered-saline (PBS) with a pH at 7.2 was used as mobile phase during column loading. Elution happened with a buffer containing glycine, arginine and sodium chloride at pH 2.3. Flow was set to 0.6 ml throughout the whole experiment. Peak detection was carried out with a fluorescence detector (FLD) at 280 nm excitation and 350 nm emission (280 nm→350 nm), the UV detection was at 280 nm.

Results: FIG. 10 shows the comparison of the same sample detected by fluorescence and UV. The peak area measured by fluorescence is roughly 20 times bigger than the peak area by UV detection.

Interpretation: Capsid detection by fluorescence shows an advantage as compared to detection via UV. Since the signal is more intense, capsids can be detected with fluorescence even if the UV signal is not strong enough to generate a peak bigger than background noise. This indicates a lower limit of detection and is an advantage during analytical measurements.

Example 10: "Comparison to Prior Art Methods"

Experimental details: The developed method was compared to different prior art analytical methods, which are SEC-MALS (Wyatt Technology), ELISA (Progen Kits for AAV2, AAV5 and AAV8) and ddPCR (Biorad QX200). To allow the comparison, aliquots of the same AAV8, AAV5 and AAV2 samples were used and SEC-MALS, ELISA and ddPCR were applied using the methods specified above and in the respective protocols of the supplier. The quantification of AAV capsid titers and AAV genomic titers using the developed method was performed as described above, e.g. in Example 2 and Example 7. The AAV samples were generated from cell culture medium. Cells and debris were removed by filtration or clarification (protocol 1 or 2, respectively). In order to receive purified extract, a buffer exchange was applied to the crude sample. SEC-MALS is better applied using purified rather than crude samples; see the table shown in FIG. 11 which displays no SEC-MALS results for most crude samples.

Results: Overall, the results show that the developed method can be used as comparison for all tested AAV serotypes, as well as for crude and for purified samples. The results are shown in FIG. 11. Furthermore, it could be shown that the invented method can not only be used for direct analysis, but also subsequent methods like SEC-MALS can be applied. The difference of a cleaned or purified sample applying the method described herein vs. a filtered sample is depicted in FIGS. 12 and 13.

Interpretation: The results show that the developed method can be used for a range of purified and crude samples, while SEC-MALS is limited to purified samples; see FIGS. 12 and 13. Those results also show that the AAV integrity is not compromised by the invented method. Also, the ELISA needs to be chosen in order fit the serotype, the ddPCR has to be adapted to the vector genome sequence and only a combination of ELISA and ddPCR allows the analysis of the full vs. empty AAV. In contrast, the developed method allows to get all results with one set up, one sample and one run. This is highly advantageous compared to other methods.

The invention claimed is:

1. An affinity chromatography method for the detection of the capsid titer of an adeno-associated virus (AAV), wherein the method comprises the following steps:
   (a) loading an AAV sample onto an affinity matrix with a sample volume of between 1 μl and 1500 μl (1.5 ml);
   (b) eluting the AAV from the affinity matrix; and
   (c) detecting the AAV capsid titer in the eluate with a fluorescence detection system, wherein the fluorescence detection system comprises detection of the AAV in the eluate at an emission wavelength of between 320 nm and 350 nm and at excitation wavelength of between 200 and 290 nm, thereby determining intrinsic fluorescence of aromatic amino acids in the AAV capsid proteins.

2. The method of claim 1, wherein the AAV sample is a non-purified sample.

3. The method of claim 1, wherein the AAV sample comprises crude cell culture broth, cell lysate, and/or a cell supernatant from a cell culture producing AAV.

4. The method of claim 1, wherein the AAV sample comprises a mixture comprising AAV capsids containing a complete genome (full capsids), partially-filled capsids, empty capsids and aggregates.

5. The method of claim 1, further comprising quantifying the eluate comprising the AAV by a UV spectrophotometry method.

6. The method of claim 1, wherein the affinity matrix is packed into a chromatography column.

7. The method of claim 6, wherein the chromatography column is a high-performance liquid chromatography column.

8. The method of claim 6, wherein the chromatography column comprises a volume that ranges between 20 and 1000 mm$^3$.

9. The method of claim 6, wherein the column is packed with an affinity matrix volume of between 1 μl and 5 ml.

10. The method of claim 6, wherein the operating pressure of the column is above 15 bar.

11. The method of claim 10, wherein the operating pressure of the column is between 15 bar and 400 bar.

12. An affinity chromatography method for the determination of the ratio of full and empty capsids of an adeno-associated virus (AAV), wherein the method comprises the following steps:
   (a) loading an AAV sample onto an affinity matrix with a sample volume of between 1 μl and 1500 μl (1.5 ml);
   (b) eluting the AAV from the affinity matrix; and
   (c) detecting simultaneously the AAV capsid titer in the eluate with a fluorescence detection system and the AAV genomic titer with a UV spectrophotometry method thereby determining the ratio of full and empty capsids of the AAV, wherein the fluorescence detection system comprises the detection of the AAV in the eluate at an emission wavelength of between 320 nm and 350 nm and at excitation wavelength of between 200 and 290 nm, thereby determining the intrinsic fluorescence of the aromatic amino acids in the AAV capsid proteins.

13. The method of claim 12, wherein the AAV sample is a non-purified sample.

14. The method of claim 12, wherein the AAV sample comprises crude cell culture broth, cell lysate, and/or a cell supernatant from a cell culture producing AAV.

15. The method of claim 12, wherein the AAV sample comprises a mixture comprising AAV capsids containing a complete genome (full capsids), partially-filled capsids, empty capsids and aggregates.

16. The method of claim 12, wherein the UV spectrophotometry method comprises determining the AAV in the eluate at 260 nm.

17. The method of claim 12, wherein the affinity matrix is packed into a chromatography column.

18. The method of claim 17, wherein the chromatography column is a high-performance liquid chromatography column.

19. The method of claim 17, wherein the chromatography column comprises a volume that ranges between 20 and 1000 mm$^3$.

20. The method of claim 17, wherein the column is packed with an affinity matrix volume of between 1 μl and 5 ml.

21. The method of claim 17, wherein the operating pressure of the column is above 15 bar.

22. The method of claim 21, wherein the operating pressure of the column is between 15 bar and 400 bar.

* * * * *